US008328784B2

(12) United States Patent
Jensen et al.

(10) Patent No.: US 8,328,784 B2
(45) Date of Patent: *Dec. 11, 2012

(54) SYSTEMS AND METHODS FOR DELIVERY OF PERITONEAL DIALYSIS (PD) SOLUTIONS

(75) Inventors: Lynn E. Jensen, Syracuse, UT (US); Spencer Clark, Kaysville, UT (US); Olli Tuominen, Hong Kong (CN); Jay M. Lan, Thousand Oaks, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 268 days.

This patent is subject to a terminal disclaimer.

(21) Appl. No.: 12/423,627

(22) Filed: Apr. 14, 2009

(65) Prior Publication Data

US 2009/0264854 A1 Oct. 22, 2009

Related U.S. Application Data

(63) Continuation-in-part of application No. 11/829,611, filed on Jul. 27, 2007, now Pat. No. 7,985,212, which is a continuation-in-part of application No. 11/340,403, filed on Jan. 26, 2006, now Pat. No. 7,837,666, which is a continuation-in-part of application No. 11/046,667, filed on Jan. 28, 2005, now Pat. No. 7,935,070.

(51) Int. Cl.
*B01D 11/00* (2006.01)
*A61M 37/00* (2006.01)
*A61M 5/32* (2006.01)
*A61B 19/00* (2006.01)

(52) U.S. Cl. ........... 604/416; 604/89; 604/410; 210/646

(58) Field of Classification Search .............. 604/27–30, 604/32, 190, 218, 236, 246–248, 284, 403–416
See application file for complete search history.

(56) References Cited

U.S. PATENT DOCUMENTS 2,777,443 A    1/1957   Thomas et al.
(Continued)

FOREIGN PATENT DOCUMENTS
AU         00719156 B2    5/2000
(Continued)

OTHER PUBLICATIONS

Feriani, M., et al. Bicarbonate Buffer for CAPD Solution, American Society of Artificial Organs, vol. XXXI, pp. 668-672.
(Continued)

*Primary Examiner* — Philip R Wiest
(74) *Attorney, Agent, or Firm* — Nutter McClennen & Fish LLP; David J. Powsner

(57) ABSTRACT

The invention provides container systems, kits and methods for peritoneal dialysis (PD) solutions. Such a system, for example, includes a first compartment that contains a PD osmotic agent and a second compartment that contains a PD buffer agent. The compartments maintain their respective contents separately from one another for purposes of transport, storage and/or sterilization. However, the compartments are fluidly couplable, so that their respective contents can be combined with one another, e.g., following sterilization of the agents and prior to their introduction into the patient's abdomen. The invention provides, in other aspects, such systems, kits and methods that provide protective structure which inhibits breaking of a seal prior between the second compartment and an outlet of the system, prior to breaking of a seal between the first and second compartments.

13 Claims, 19 Drawing Sheets

U.S. PATENT DOCUMENTS

| | | | |
|---|---|---|---|
| 3,557,787 A | 1/1971 | Cohen | |
| 4,132,594 A | 1/1979 | Bank et al. | |
| 4,282,863 A | 8/1981 | Beigler et al. | |
| 4,326,526 A | 4/1982 | Buck et al. | |
| 4,340,052 A | 7/1982 | Dennehey et al. | |
| 4,369,779 A | 1/1983 | Spencer | |
| 4,396,383 A | 8/1983 | Hart | |
| 4,399,036 A | 8/1983 | Babb et al. | |
| 4,403,992 A | 9/1983 | Bertellini et al. | |
| 4,458,733 A | 7/1984 | Lyons | |
| 4,458,811 A | 7/1984 | Wilkinson | |
| 4,465,488 A | 8/1984 | Richmond et al. | |
| 4,467,588 A | 8/1984 | Carveth | |
| 4,484,920 A | 11/1984 | Kaufman et al. | |
| 4,489,535 A | 12/1984 | Veltman | |
| 4,496,361 A | 1/1985 | Kilkson | |
| 4,516,977 A | 5/1985 | Herbert | |
| 4,548,605 A | 10/1985 | Iwamoto et al. | |
| 4,561,110 A | 12/1985 | Herbert | |
| 4,584,176 A | 4/1986 | Oliver et al. | |
| 4,608,043 A | 8/1986 | Larkin | |
| 4,630,727 A * | 12/1986 | Feriani et al. | 206/221 |
| 4,663,166 A | 5/1987 | Veech | |
| 4,753,697 A | 6/1988 | Shaposka et al. | |
| 4,756,838 A | 7/1988 | Veltman | |
| 4,761,237 A | 8/1988 | Alexander et al. | |
| 4,863,714 A | 9/1989 | Sovak et al. | |
| 4,879,280 A | 11/1989 | Seyffart et al. | |
| 4,959,175 A | 9/1990 | Yatzidis et al. | |
| 5,011,826 A | 4/1991 | Steudle et al. | |
| 5,039,609 A | 8/1991 | Klein | |
| 5,071,558 A | 12/1991 | Itoh et al. | |
| 5,141,492 A | 8/1992 | Dadson et al. | |
| 5,211,643 A | 5/1993 | Reinhardt et al. | |
| 5,279,605 A | 1/1994 | Karrasch et al. | |
| 5,296,242 A | 3/1994 | Zander et al. | |
| 5,336,173 A | 8/1994 | Folden | |
| 5,343,395 A | 8/1994 | Watts | |
| 5,383,324 A | 1/1995 | Segers et al. | |
| 5,423,421 A | 6/1995 | Inoue et al. | |
| 5,431,496 A | 7/1995 | Balteau et al. | |
| 5,462,526 A | 10/1995 | Barney et al. | |
| 5,509,898 A | 4/1996 | Isono et al. | |
| 5,536,469 A | 7/1996 | Jonsson et al. | |
| 5,560,403 A | 10/1996 | Balteau et al. | |
| 5,562,836 A * | 10/1996 | Joie et al. | 210/782 |
| 5,610,170 A | 3/1997 | Inoue et al. | |
| 5,694,978 A | 12/1997 | Heilmann et al. | |
| 5,706,937 A | 1/1998 | Futagawa et al. | |
| 5,713,850 A | 2/1998 | Heilmann et al. | |
| 5,744,027 A | 4/1998 | Connell et al. | |
| 5,761,673 A | 6/1998 | Bookman et al. | |
| 5,783,269 A | 7/1998 | Heilmann et al. | |
| 5,820,582 A | 10/1998 | Keilman | |
| 5,827,820 A | 10/1998 | duMoulin et al. | |
| 5,853,388 A | 12/1998 | Semel | |
| 5,871,477 A | 2/1999 | Isono et al. | |
| 5,891,092 A | 4/1999 | Castellano | |
| 5,928,213 A * | 7/1999 | Barney et al. | 604/410 |
| 5,945,129 A | 8/1999 | Knerr et al. | |
| 5,945,449 A | 8/1999 | Purcell et al. | |
| 6,004,636 A | 12/1999 | Nicola et al. | |
| 6,012,578 A | 1/2000 | Keilman | |
| 6,013,294 A | 1/2000 | Bunke et al. | |
| 6,017,598 A | 1/2000 | Kreischer et al. | |
| 6,023,714 A | 2/2000 | Hill et al. | |
| 6,039,719 A | 3/2000 | Wieslander et al. | |
| 6,039,720 A | 3/2000 | Wieslander | |
| 6,122,325 A | 9/2000 | Mogre et al. | |
| 6,123,847 A | 9/2000 | Bene | |
| 6,139,754 A | 10/2000 | Hartranft et al. | |
| 6,196,991 B1 | 3/2001 | Keilman | |
| 6,241,943 B1 | 6/2001 | Wieslander et al. | |
| 6,277,815 B1 | 8/2001 | Knerr et al. | |
| 6,284,140 B1 | 9/2001 | Sommermeyer et al. | |
| 6,300,947 B1 | 10/2001 | Kanevsky | |
| 6,309,673 B1 | 10/2001 | Duponchelle et al. | |
| 6,348,049 B1 | 2/2002 | Spencer | |
| 6,379,340 B1 | 4/2002 | Zinger et al. | |
| 6,399,110 B1 | 6/2002 | Kikuchi et al. | |
| 6,475,529 B2 | 11/2002 | Duponchelle et al. | |
| 6,508,800 B1 | 1/2003 | Keilman et al. | |
| 6,610,206 B1 | 8/2003 | Callan et al. | |
| 6,645,191 B1 | 11/2003 | Knerr et al. | |
| 6,764,482 B2 | 7/2004 | Keilman et al. | |
| 6,875,203 B1 * | 4/2005 | Fowles et al. | 604/403 |
| 6,911,014 B2 * | 6/2005 | Wentling et al. | 604/29 |
| 7,004,924 B1 | 2/2006 | Brugger et al. | |
| 7,011,855 B2 | 3/2006 | Martis et al. | |
| 7,029,465 B2 | 4/2006 | Heyes et al. | |
| 7,035,696 B1 | 4/2006 | Sadeghi et al. | |
| 7,038,147 B2 | 5/2006 | Sasanouchi et al. | |
| 7,040,963 B1 | 5/2006 | Okuda et al. | |
| 7,040,975 B2 | 5/2006 | Shefet et al. | |
| 7,044,877 B2 | 5/2006 | Ai | |
| 7,053,059 B2 | 5/2006 | Zieske et al. | |
| 7,053,683 B2 | 5/2006 | Li | |
| 7,122,210 B2 | 10/2006 | Elisabettini et al. | |
| 7,134,966 B1 | 11/2006 | Tice | |
| 7,134,996 B2 | 11/2006 | Bardy | |
| 7,188,151 B2 | 3/2007 | Kumar et al. | |
| 7,215,991 B2 | 5/2007 | Besson et al. | |
| 7,678,097 B1 | 3/2010 | Peluso et al. | |
| 7,837,666 B2 * | 11/2010 | Jensen et al. | 604/416 |
| 7,935,070 B2 | 5/2011 | Jensen et al. | |
| 7,985,212 B2 | 7/2011 | Jensen et al. | |
| 8,052,631 B2 | 11/2011 | Jensen et al. | |
| 2001/0049158 A1 | 12/2001 | Warner et al. | |
| 2003/0150748 A1 | 8/2003 | Crawley | |
| 2003/0159953 A1 | 8/2003 | Linden et al. | |
| 2003/0232093 A1 | 12/2003 | Faict et al. | |
| 2004/0118789 A1 | 6/2004 | Rothman et al. | |
| 2004/0121982 A1 | 6/2004 | Martis et al. | |
| 2005/0020507 A1 | 1/2005 | Zieske et al. | |
| 2005/0224372 A1 | 10/2005 | Sasso et al. | |
| 2006/0172954 A1 | 8/2006 | Jensen et al. | |
| 2006/0182814 A1 | 8/2006 | Martis et al. | |
| 2006/0186045 A1 | 8/2006 | Jensen et al. | |
| 2007/0106205 A1 | 5/2007 | Connell et al. | |
| 2007/0112603 A1 | 5/2007 | Kauthen et al. | |
| 2008/0000835 A1 | 1/2008 | Rogers | |
| 2008/0027374 A1 | 1/2008 | Jensen et al. | |
| 2008/0045884 A1 | 2/2008 | Landherr et al. | |
| 2008/0177222 A1 | 7/2008 | Roger | |
| 2008/0177243 A1 | 7/2008 | Roger | |
| 2008/0183126 A1 | 7/2008 | Landherr et al. | |
| 2008/0183127 A1 | 7/2008 | Landherr et al. | |
| 2009/0076856 A1 | 3/2009 | Darby et al. | |
| 2009/0078592 A1 | 3/2009 | Jensen et al. | |
| 2009/0264854 A1 | 10/2009 | Jensen et al. | |
| 2010/0049158 A1 | 2/2010 | Roger | |
| 2012/0095392 A1 | 4/2012 | Jensen et al. | |

FOREIGN PATENT DOCUMENTS

| | | |
|---|---|---|
| CA | 2352561 A1 | 3/2001 |
| DE | 4122754 A1 | 1/1993 |
| DE | 04410875 A1 | 10/1995 |
| DE | 04410876 A1 | 10/1995 |
| DE | 19654746 A1 | 7/1998 |
| DE | 19748290 A1 | 5/1999 |
| DE | 69705816 T2 | 4/2002 |
| EA | 0564672 A1 | 10/1993 |
| EP | 0022922 A1 | 1/1981 |
| EP | 0038355 A1 | 10/1981 |
| EP | 076355 A2 | 4/1983 |
| EP | 0083360 A1 | 7/1983 |
| EP | 0165933 A1 | 1/1986 |
| EP | 0209607 A1 | 1/1987 |
| EP | 0249667 A1 | 12/1987 |
| EP | 0278100 A2 | 8/1988 |
| EP | 0339549 A2 | 11/1989 |
| EP | 0399549 A1 | 11/1990 |
| EP | 0399670 | 11/1990 |
| EP | 0437274 A1 | 7/1991 |
| EP | 0439061 A1 | 7/1991 |
| EP | 0456806 A1 | 11/1991 |
| EP | 0490307 A2 | 6/1992 |

| | | | |
|---|---|---|---|
| EP | 0564672 A1 | 10/1993 |
| EP | 0613688 A1 | 9/1994 |
| EP | 0626857 A1 | 12/1994 |
| EP | 0776649 A2 | 6/1997 |
| EP | 00857075 A1 | 8/1998 |
| EP | 0857075 A1 | 8/1998 |
| EP | 0857075 B1 | 8/1998 |
| EP | 0935967 A2 | 8/1999 |
| EP | 1008341 A1 | 6/2000 |
| EP | 1131077 A1 | 9/2001 |
| EP | 1561448 A1 | 8/2005 |
| FR | 2467599 A1 | 4/1981 |
| FR | 2735099 A1 | 12/1996 |
| JP | 56164113 A | 12/1981 |
| JP | 63-065874 A | 3/1988 |
| JP | 2304026 A | 12/1990 |
| JP | 3195561 A | 8/1991 |
| JP | 5105633 A | 4/1993 |
| JP | 6105905 A | 4/1994 |
| JP | 06504708 T | 6/1994 |
| JP | 7252137 A | 10/1995 |
| JP | 08089571 A | 4/1996 |
| JP | 8131542 A | 5/1996 |
| JP | 8164199 A | 6/1996 |
| JP | 9087182 A | 3/1997 |
| JP | 9110703 A | 4/1997 |
| JP | 09239023 A | 9/1997 |
| JP | 09299476 A | 11/1997 |
| JP | 9301875 A | 11/1997 |
| JP | 10201821 A | 8/1998 |
| JP | 11004872 A | 1/1999 |
| JP | 11009659 A | 1/1999 |
| JP | 11019178 A | 1/1999 |
| JP | 11070166 A | 3/1999 |
| JP | 11226120 A | 8/1999 |
| JP | 2003520632 T | 7/2003 |
| JP | 2003339853 A | 12/2003 |
| TR | 9701278 T1 | 7/1998 |
| WO | WO-83/00087 A1 | 1/1983 |
| WO | WO-85/01657 A1 | 4/1985 |
| WO | WO-86/03407 A1 | 6/1986 |
| WO | WO-87/03809 A1 | 7/1987 |
| WO | WO-91/08008 A2 | 6/1991 |
| WO | WO-91/18610 A1 | 12/1991 |
| WO | WO-93/09820 A1 | 5/1993 |
| WO | WO-9309822 A1 | 5/1993 |
| WO | WO-93/19792 A1 | 10/1993 |
| WO | WO-94/25084 A1 | 11/1994 |
| WO | WO-95/19778 A1 | 7/1995 |
| WO | WO-96/01118 A1 | 1/1996 |
| WO | WO-97/05851 A1 | 2/1997 |
| WO | WO-97/06810 A1 | 2/1997 |
| WO | 97/07837 A1 | 3/1997 |
| WO | WO-97/41902 A1 | 11/1997 |
| WO | WO-98/10733 A1 | 3/1998 |
| WO | WO-99/01144 A1 | 1/1999 |
| WO | WO-99/09953 A1 | 3/1999 |
| WO | WO-0117534 A1 | 3/2001 |
| WO | WO-0142758 A2 | 6/2001 |
| WO | WO-2006083653 A2 | 8/2006 |
| WO | WO-2006122325 A2 | 11/2006 |
| WO | WO-2006125198 A2 | 11/2006 |
| WO | WO-2007035696 A1 | 3/2007 |
| WO | WO-2007038147 A2 | 4/2007 |
| WO | WO-2007040963 A2 | 4/2007 |
| WO | WO-2007040975 A2 | 4/2007 |
| WO | WO-2007044877 A2 | 4/2007 |
| WO | WO-2007053683 A2 | 5/2007 |
| WO | WO-2009017472 A1 | 2/2009 |

OTHER PUBLICATIONS

Feriani, Mariano, et al., Clinical Experience with a 39 MMOL/L Bicarbonate-Buffered Peritoneal Dialysis Solution, Peritoneal Dialysis International, vol. 17, pp. 17-21.

Feriani, Mariano, et al., Short-Term Clinical Study with Bicarbonate-Containing Peritoneal dialysis Solution, Peritoneal Dialysis International, vol. 13, pp. 196-301.

Lactate-Containing versus Bicarbonate-Containing Peritoneal Dialysis Solutions, Peritoneal Dialysis International, vol. 12, pp. 276-277.

Lindley, Elizabeth MD., Should Dialysis Fluid Composition be Individualised? NHS Trust, Renal and Liver Services, St. James's University Hospital, Leeds, UK.

Martinson, Kjellstrand P., et al., Degradation in Peritoneal Dialysis Fluids May be Avioded by Using Low pH and high glucose Concentration, Perit Dial Int., Jul.-Aug. 2001, 21(4), pp. 338-344.

Morgan, L.W., et al., Glucose Degradation Products (GDP) Retard Remesothelialization Independently ofd-Glucose Concentration, Ingenta Article Summary, Research Article ISSN: 0085-2538, Blackwell Publishing.

Nilsson-Thorell, C.B., et al., Heat Sterilization of Fluids for Peritoneal Dialysis Gives Rise to Aldehydes, Peritoneal Dialysis International, Journal of the Int. Soc. for Peritoneal Dialysis (Canada) 1993, 13 (3) pp. 208-213 (abstract only).

Palmer, Biff E., Dialysate Composition in Hemodialysis and Peritoneal Dialysis, Dialysate Composition in Hemodialysis and Peritoneal Dialysis, Chapter 2, 8 pages.

Parker,Tom F., Practical Applications of Technical Advances in Hemodialysis Therapy, Seminars in Dialysis, vol. 12, Suppl. 1 May-Jun. 1999, pp. S45-S49.

Reduced Glucose Degradation Products in Bicarbonate/Lactate-Buffered Peritoneal Dialysis Solutions Produced in Two-Chamberd Bags, Perit Dial Int., Jul.-Aug. 1997 17(4): 373-8.

Schambye, Hans Thalsgard, The Cytoxicity of Continuous Ambulatory Peritoneal Dialysis Solutions with Different Bicarbonate/Lactate Ratios, Peritoneal Dialysis International, vol. 13, Supplement 3, pp. S116-S118.

Tjiang, Boen San MD, Peritoneal Dialysis, A Clinical Study of Factors Governing its Effectiveness, Van Gorcum & Comp., N.V. ASSEN-MCMLIX, Medical Library No. 161, pp. 75-77.

Treatment Methods for Kidney Failure: Peritoneal Dialysis, National Kidney and Urologic Diseases Information Clearinghouse, Bethesda MD., 20 pages.

Graham, Kenneth A., Correction of Acidosis in Hemodialysis Patients Increases the Sensitivity of the Parathyroid Glands to Calcium, Journal of the American Society of Nephrology, 1997, Sep. 30, 1996.

Japanese Office Action, Application No. 512574/08, Mailed Mar. 2, 2010, 12 pages.

Nissenson, Richard, N, Fine, Dominick E, Gentile (Chapter author is Richard Ward), Clinical Dialysis, Chapter 21: Acid Base Homeostasis, 1995, pp. 495-517.

International Search Report and Written Opinion mailed Jan. 4, 2012, for Application No. PCT/US20111052699 (12 Pages).

Extended European Search Report issued Feb. 22, 2012 for Application No. 07836291.0 (6 Pages).

Acidosis: Targe Bicarbonate Levels, The CARI Guidelines—Caring for Australians with Renal Impairment, Biochemical and Haematological Targets, Mar. 2000.

Alscher, Dominik M. et al., A New Lactate-Based, Plasticizer-Free, Neutral Peritoneal Dialysis Fluid Provided in a Two-Compartment System: Effecct on Peripheral Leukocyte Function, Nephron 2000, 86, pp. 62-69.

ASAIO, American Society for Artificial Internal Organs, 1994 Abstracts, 490th Anniversary Meeting, San Francisco, 4 pages.

Based on: Lage C., et al., First in Vitro and In Vivo Experiences with Staysafe Balance, a pH-Neutral Solution in a Dual-Chambered Bag, Pent Dial Int. 20 (S5), 2000, pp. 28-32.

Blair, D., Nutritional Effects of Delivered Bicarbonate Dose in Maintenance Hemodialysis Patients, Journal of Renal Nutrition, vol. 13, No. 3 Jul. 2003, pp. 205-211.

Budavari, Susan, et al., The Merck Index, Twelfth Edition, 1996, pp. 1471-1472.

Buoncristiani et al,. Autosterilizing CAPD Connection Systems, Nephron 35: 244-247 (1983).

Cancarini, Giovanni C., Clinical Evaluation of a Peritoneal Dialysis Solution with 33 mmol/L Bicarbonate, Peritoneal Dialysis International, vol. 18, pp. 576-582.

Carozzi, et al., Biocompatibility Study on Peritoneal Dialysis Solution Bags for CAPD, American Society for Artificial Organs, vol. XXXI, 1985, 7 pages.

Comstock, Thomas J., Renal Dialysis, Applied Therapeutics: The Clinical Use of Drugs, Applied Therapeutics, Inc. Vancouver, WA, 1995.

Crawford-Bonadio, et al., Comparison of Peritoneal Dialysis Solutions, Nephrology Nursing Journal, Sep.-Oct. 2004, vol. 31, No. 5, pp. 500-520.

Erixon, Martin, et al., PD Fluids Contain High Concentrations of Cytotoxic GPD's Direcctly After Sterilization, Peritoneal Dialysis (Canada) Jul.-Aug. 2004, 24(4) pp. 392-398 (abstract only).

Faller, Bernadette, et al., Loss of Ultrafiltration in Continuous Ambulatory Peritoneal Dialysis: A Role for Acetate, Peritoneal Dialysis Bulletin, Jan.-Mar. 1984, pp. 10-13.

Feriani, Individualized bicarbonate concentrations in the peritoneal dialysis fluid to optimize acid-base status in CAPD patients. Nephrol Dial Transplant (2004) 19: 195-202.

Feriani, M., et al. Bicarbonate Buffer for CAPD Solution, American Society of Artificial Organs, vol. XXXI, pp. 668-672. 1985.

Feriani, Mariano MD, et al., The Acid-Base Effects of Peritoneal Dialysis, Current Opinion in Critical Care, Fulltext: vol. 5(6) Dec. 1999, pp. 448-451.

Feriani, Mariano, Buffers: Bicarbonate, lactate and Pyruvate, Kidney International, vol. 50, Suppl. 56 (1996), pp. S-75-S-80.

Feriani, Mariano, et al., Clinical Experience with a 39 MMOL/L Bicarbonate-Buffered Peritoneal Dialysis Solution, Peritoneal Dialysis International, vol. 17, pp. 17-21, 1997.

Feriani, Mariano, et al., Randomized Long-Term Evaluation of Bicarbonate-Buffered CAPD Solution, Kidney International, vol. 54 (1998), pp. 1731-1738.

Feriani, Mariano, et al., Short-Term Clinical Study with Bicarbonate-Containing Peritoneal dialysis Solution, Peritoneal Dialysis International, vol. 13, pp. 196-301, 1993.

Franz, Hans Eduard, Blutreinigungsverfahren Technik and Klinik, Georg Thieme Verlag Stuttgart, New York 1990.

Gagnor, R.F., et al. Effect of Euhydric Peritoneal Dialysis Solution (PDS) Containing a Mixture of Bicarbonate and Lactate on Neutrophilic Superoxide Production, American Society for Artificial Internal Organs , 1994 Abstracts, 40th Anniversary Meeting Apr. 14-16, 1994, San Francisco Hilton, San Francisco, CA.

Graham, Kenneth A., Correction of Acidosis in Hemodialysis Decreases Whole-Body Protein Degradation, Journal of theThe American Society of Nephrology, 1997, Jul. 3, 1996.

Hekking L.H., Effect of PD Fluid Instillation on the Peritonitis-Induced Influx and Bacterial Clearing Capacity of Peritoneal Cells, Nephrology, Dialysis, Transplantation, Official Publication of the European Dialysis and Transplant Assoication, (England) Mar. 2001, 16(3) pp. 679-682 (abstract only).

Hollon, J. & Ward, R. Acid-Base Homeostasis in Dialysis Patients, Clinical Dialysis, Chap. 20, pp: 553-575, Sep. 1990.

Ing, T.S., et al., Bicarbonate-Buffered Peritoneal Dialysis, The International Journal of Artificial Organs, vol. 8 No. 3, May 1985, pp. 121-124.

Ing, T.S., et al., Preparation of Bicarbonate-Containing Dialysate for Peritoneal Dialysis, Hines-Loyola Medical Center, Jul. 1983, pp. 217-218.

Ing, T.S., MD., Lactate-Containing Peritoneal Dialysis Solutions, Department of Midicine Veterans Affairs Hospital, Wichlig Editore, 1993, pp. 688-693.

International Search Report and Written Opinion, International Application No. PCT/US06/02674, Mailed Sep. 25, 2007.

International Search Report, International Application No. PCT/US07/016906, Mailed Jul. 31, 2008.

Jarkelid, L.E., et al., In Vitro Cytotoxicity of Four Different Buffers for Use in Peritoneal Dialysis, ATLA Alternatives to Laboratory Animals, United Kingdom, 2000, 28/3, pp. 415-425 (abstract only).

Jonasson P., et al., Heat-Sterilized PD Fluid Blocks Leukocyte Adhesion and Increases Flow Velocity in Rat Peritoneal Venules, Peritoneal Dialysis (Canada) 1996, 16 Suppl 1, pp. PS137-PS140 (abstract only).

Jonasson P., et al., Peritoneal Leukocyte Survival and Respiratory Burst Responses in Patients Treated with a Low Glucose Degradation and High pH Peritoneal Dialysis Fluid, International Journal of Artificial Organs (Italy) Feb. 2003, 26(2) pp. 121-128 (abstract only).

Kjellstrand, et al., Temperature: The Single Most Important Factor for Degradation of Glucose Fluids During Storage, Peritoneal Dialysis International, Journal of the Int. Soc. for Peritoneal Dialysis (Canada) Jul.-Aug. 2004, 24(4) pp. 385-391 (abstract only).

Kjellstrand, P., et al., Development of Toxic Degradation Products During Heat Sterilization of Glucose-Containing Fluids for Peritoneal Dialysis, Influence of Time and Temperature, Peritoneal Dialysis International, Journal of the Int. Soc. for Peritoneal Dialysis (Canada) 1995, 15 (1) pp. 26-32 (abstract only).

Lactate-Containing versus Bicarbonate-Containing Peritoneal Dialysis Solutions, Peritoneal Dialysis International, vol. 12, pp. 276-277, 1992.

Lai, K.N., et al. Differential Expression of Receptors for Advanced Glycation and End-Products in Peritoneal Mesothelial Cells Exposed to Glucose Degration Products, Clinical and Experimental Immunology (England) Dec. 2004, 138 (3) pp. 466-475 (abstract only).

Leung, Joseph et al., Glucose Degradation Products Downregulate Z0-1 Expression in Human Peritoneal Mesothelial Cells: The role of VEGF, Nephrology, Dialysis, Transplantation, Official Publication of the European Dialysis and Transplant Association, Jul. 2005, 20 (7) pp. 1336-1349 (abstract only).

Linden, T. et al., 3,4 Dideoxyglucosone-3-3ne, (3,4-DGE): a Cytotoxic Glucose Degradation Product in Fluids for Peritoneal Dialysis, Kidney International, Aug. 2002, 62 (2) pp. 697-703.

Linden, T., 3-Dexyglucosone, a Promoter of Advanced Glycation End Products in Fluids for Peritoneal Dialysis, Peritoneal Dialysis International, Journal of the International Society for Peritoneal Dialysis, May-Jun. 1998 (3) pp. 290-293.

Linden, T., et al., Glucose Degradation Products in Peritoneal Dialysis Fluids May Have Both Local and Systemic Effects: A Study of Residual Fluid and Mesothelial Cells, Peritoneal Dialysis International, Journal of the Int. Soc. for Peritoneal Dialysis (Canda) Nov.-Dec. 2001, 21 (6) pp. 607-610 (abstract only).

Lindley, Elizabeth MD., Should Dialysis Fluid Composition be Individualised? NHS Trust, Renal and Liver Services, St. James's University Hospital, Leeds, UK, 1998.

Mactier, Robert A. et al., Bicarbonate and Bicarbonate/Lactate Peritoneal Dialysis Solutions for the Treatment of Infusion Pain, Kidney International, vol. 53 (1998) pp. 1061-1067.

Manahan, Ferdinand J., Effects of Bicarbonate-Containing Versus Lactate-Containing Peritoneal Dialysis Solutions on Superoxide Production by Human Neutrophils, Artificial Organs, vol. 13, No. 6, 1989, pp. 495-497.

Martinson E., Toxicity of Heat Sterilized Peritoneal Dialysis Fluids Is Derived from Degradation of Glucose, ASAIO Journal (American Society for Artifical Internal Organs) Jul.-Sep. 1992, 38(3) pm370-2 (abstract only).

Martinson, Kjellstrand P., et al., Degradation in Peritoneal Dialysis Fluids May be Avioded by Using Low pH and high glucose Concentration, Perit Dial Int., Jul.-Aug. 2001 21(4), pp. 338-344.

Morgan, L.W., et al., Glucose Degradation Products (GDP) Retard Remesothelialization Independently ofd-Glucose Concentration, Ingenta Article Summary, Research Article ISSN: 0085-2538, Blackwell Publishing, 2003.

Musi B., et al., Very High Daily Intraperitoneal Doses of Carbonyl Compounds Affect the Morphology, but not the Exchange Characteristics, of Rat Peritoneum, Blood Purification (Switzerland) 2001, 19 (3) pp. 286-292 (abstract only).

Musi, B., Effects of Acidity, Glucose Degradation Products, and Dialysis Fluid Buffer Choice on Peritoneal Solute and Fluid Transport in Rats, Peritoneal Dialysis International, Journal of the Int. Soc. for Peritoneal Dialysis (Canada) May-Jun. 1988, 18(3) pp. 303-310 (abstract only).

Musi, B., et al, Biocompatibility of Peritoneal dialysis Fluids: Long-Term Exposure of Nonumeric Rats, Peritoneal Dialysis International (Canada) 2004, 24/1 pp. 37-47.

Nilsson-Thorell, C.B., et al., Heat Sterilization of Fluids for Peritoneal Dialysis Gives Rise to Aldehydes, Peritoneal Dialysis International, Journal of the Int. Soc. for Peritoneal Dialysis (Canada) 1993, 13 (3) pp. 208-213 (abstract only), 1950.

Odel, Howard M., et al.., Peritoneal Lavage as an Effective Means of Extrarenal Excretion, American Journal of Medicine, vol. 9, pp. 63-77.

Oh, Man S., MD., What Unique Acid-Base Considerations Exist in Dialysis Patients? Seminars in Dialysis, vol. 17, No. 5 Sep.-Oct. 2004, pp. 351-354.

Palmer, Biff E., Dialysate Composition in Hemodialysis and Peritoneal Dialysis, Dialysate Composition in Hemodialysis and Peritoneal Dialysis, Chapter 2, 8 pages. 2004.

Parker, Tom F., Practical Applications of Technical Advances in Hemodialysis Therapy, Seminars in Dialysis, vol. 12, Suppl. 1 (May-Jun.) 1999, pp. S45-S49.

Reduced Glucose Degradation Products in Bicarbonate/Lactate-Buffered Peritoneal Dialysis Solutions Produced in Two-Chamberd Bags, Perit Dial Int., Jul.-Aug. 1997, 17(4): 373-8.

Richardson, Robert et al., Bicarbonate, L-Lactate and D-Lactate Balance in Intermittent Peritoneal Dialysis, Peritoneal Dialysis Bulletin, vol. 6, No. 4, Oct.-Dec. 1986.

Rippe B., et al., Clinical and Physiological Effects of a New, Less Toxic and Less Acidic Fluid for Peritoneal Dialysis, Peritoneal Dialysis International, Journal of the International Society for Peritoneal Dialysis (Canada) Jan.-Feb. 1997, 17 (1) pp. 27-34 (abstract only).

Rippe, B. et al., "Long-term Clinical Effects of a Peritoneal Dialysis Fluid With Less Glucose Degradation Products," Kidney Intl 59(1):348-57 (Jan. 2001).

Ronco C., et al., Fluid Composition for CRRT, Sepsis, Kidney and Multiple Organ Dysfunction, Contrib Nephrol Basel, Karger, 2004, vol. 144, pp. 222-227.

Ronco, C. et al., Dialysate/Infusate Buffer Modulation in Dialysis, Contrib. Nephrol Basel, Karger, 2002, vol. 137, pp. 357-363.

Ronco, C., et al., Buffer Content in Automated Peritoneal Dialysis Solutions, Automated Peritoneal Dialysis, Contrib Nephrol, Basel, Karger, 1999, vol. 129, pp. 187-194.

Sam, R. et al., "Composition and clinical use of hemodialysates," Hemodialysis Intl. 10:15-28 (2006).

Schambye, Hans T., et al., Bicarbonate-Versus Lactate-Based CAPD Fluids: A Biocompatibility Study in Rabbits, Peritonial Dialysis International, vol. 12, pp. 281-286. (1992).

Schambye, Hans Thalsgard et al., The Cytoxicity of Continuous Ambulatory Peritoneal Dialysis Solutions with Different Bicarbonate.Lactate Ratios, Peritoneal Dialysis International, vol. 13, Supplement 2, 1993, pp. S116-S118.

Schambye, Hans Thalsgard, The Cytoxicity of Continuous Ambulatory Peritoneal Dialysis Solutions with Different Bicarbonate/Lactate Ratios, Peritoneal Dialysis International, vol. 13, Supplement 3, pp. S116-S118, 1993.

Schroder, Cornelis H. MD, The Choice of Dialysis Solutions in Pediatric Chronic Peritoneal Dialysis: Guidelines by an Ad Hoc European Committee, Perit Dial Int, 2001, 21: 568-574.

Scientific Abstracts Gambrosol Trio, Doc./Info Dept., Lyon, France, Aug. 2004.

Simonsen, O., et al., Mass Transfer of Calcium Across the Peritoneum at Three Different Peritoneal Diaylsis Fluid CaSUP2+ and Glucose Concentrations, Kidney International, U.S., Jul. 1, 2003, 64/1, pp. 208-215 (abstract only).

Simonsen, Ole, et al., Less Infusion Pain and Elevated Level of Cancer Antigen 125 by the Use of a New and More Biocompatible PD Fluid, Advances in Peritoneal Dialysis, Vol. 12, 1996, pp. 156-160.

Tjiang, Boen San MD, Peritoneal Dialysis, A Clinical Study of Factors Governing its Effectiveness, Van Gorcum & Comp., N. V. ASSEN-MCMLIX, Medical Library No. 161, pp. 75-77, 1959.

Treatment Methods for Kidney Failure: Peritoneal Dialysis, National Kidney and Urologic Diseases Information Clearinghouse, Bethesda MD., 20 pages, 2006.

Van Bronswijk, Hans, et al., Cytotoxic Effects of Commercial Continuous AMbulatory Peritoneal Dialysis (CAPD) Fluids and of Bacterial Exoproducts on Human Mesothelial Cells in Vitro, Periotoneal Dialysis International, vol. 9, 1989, pp. 197-202.

Van Stone, John C., MD., Individualization of the Dialysate Prescription in Chonic Hemodialysis, Dialysis & Transplantation, vol. 23, No. 11, Nov. 1994, pp. 624-663.

Weislander et al., Toxicity of peritoneal dialysis fluids on cultured fibroblasts, L-929, Kidney International, vol. 40, (1991), pp. 77-79.

Weiss, L., et al., Long-Term Clinical Effets of a Peritoneal Dialysis Fluid with Less Glucose Degradation Products, Kidney International (US) Jan. 2001, 59 (1) pp. 348-357 (abstract only).

Wieslander A P., et al., Heat Sterilized PD-Fluids Impair Growth and Inflammatory Responses of Cultured Cell Lines and Human Leukocytes, Clinical Nephrology (Germany) Jun. 1993, 39(6) pp. 343-348 (abstract only).

Wieslander A.P., et al., In Vitro Biocompatibility of a Heat-Sterilized, Low-Toxic, and Less Acidic Fluid for Peritoneal Dialysis, Peritoneal Dialysis International, Journal of the Int. Soc. for Peritoneal Dialysis (Canada) 1995, 15(2), pp. 158-164 (abstract only).

Wieslander Anders, et al., Use of a Solution Comprising Glucose for Peritoneal Dialysis Having Reduced Formation of Age Products, Official Gazette of the USPTO, Patents 1247 (1): Jun. 5, 2001 (abstract only).

Wieslander, A., et al., Biological Significance of Reducing Glucose Degradation Products in Peritoneal Dialysis Fluids, Journal of the Int. Society for Peritoneal Dialysis (Canada) 2000, 20 Suppl. 5, pp. S23-S27.

Wieslander, A., et al., Cytotoxicity, pH, and Glucose Degradation Products in Four Different Brands of PD Fluid, Advances in Peritoneal Dialysis, Conference on Peritoneal Dialysis (Canada) 1996, 12 pp. 57-60 (abstract only).

Wieslander, A., et al., Glucose Degradation Products in Peritoneal Dialysis Fluids: How They Can be Avoided, Peritoneal Dialysis International, Journal of the International Society for Peritoneal Dialysis (Canada) 2001, 21 Suppl 3, pp. S119-S124 (abstract only).

Wieslander, A.P., et al., Toxicity of Effluent Peritoneal Dialysis Fluid, Advances in Peritoneal Dialysis (Canada) Conference on Peritoneal Dialysis, 1993, 9, pp. 31-35 (abstract only).

Wieslander, Anders, 3,4, Dideoxyglucosone-3-3ne, (3,4-DGE): a Cytotoxic Glucose Degradation Product in Fluids for Peritoneal Dialysis, Kidney International, Aug. 2002, 62 (2) pp. 697-703.

Wiselander, A.P., et al., Are Aldehydes in Heat-Sterilized Peritoneal Dialysis Fluids Toxic in Vitro? Peritonial Diaylysis International, Journal of the International Society for Peritoneal Dialysis (Canada) Oct.-Dec. 1995, 15 (8) pp. 348-52 (abstract only).

Wiselander, Anders et al., Bag for Containing a Sterile Medical Solution and Method of Mixing a Sterile Medical Solution, Official Gazette of the USPTO Patents 1232 (3) Mar. 21, 2000 (abstract only).

Witowski, Janusz, et al., Effect of Lactate-Buffered Peritoneal Dialysis Fluids on Human Peritoneal Mesothelial cell Interleukin-6 and Prostaglandin Systhesis, Kidney International, Vo. 46, 1994, pp. 282-293.

Yahyapour, N., et al., Protection by Glutathione of Neutrophils Against the Toxic Effects of Peritoneal Dialyis Fluid, Toxicology in Vitro-An International Journal Published in Association with BIBRA (England) Dec. 2001, 15(6) pp. 655-661 (abstract only).

Yatzidis, Hippocrates, A New Stable Bicarbonate Dialysis Solution for Peritoneal Dialysis: Preliminary Report, Nephrological Center, Peritoneal Dialysis International, vol. 11, pp. 242-227, 1991.

Zhou, X. J., et al., Effects of an Acidic, Lactate-Based Peritoneal Dialysis Solution and its Euhydric, Bicarbonate-based Counterpart on Neutrophilic Intracellular pH, The International Journal of Artificial Organs, vol. 16, No. 12, 1993, pp. 816-819.

* cited by examiner

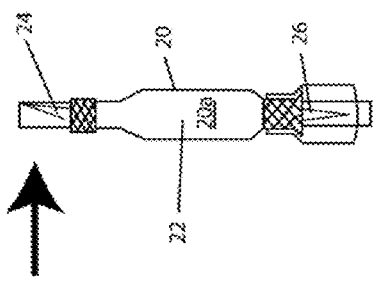
Figure 7A
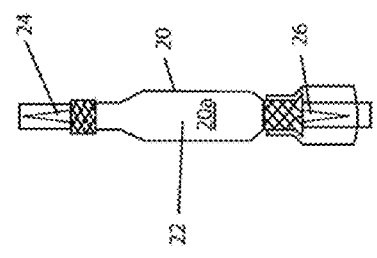
Figure 7B
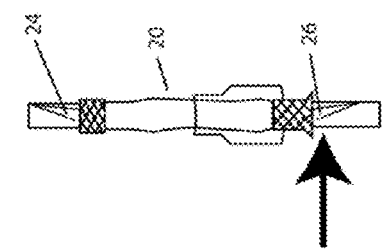
Figure 7E
Figure 7D
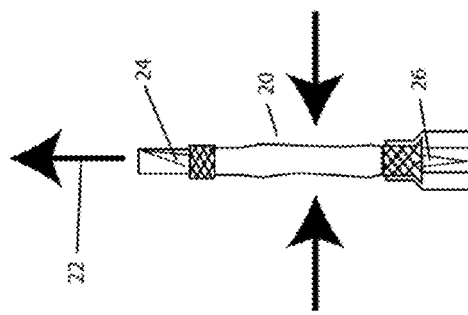
Figure 7C

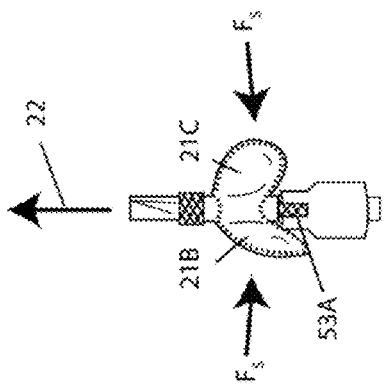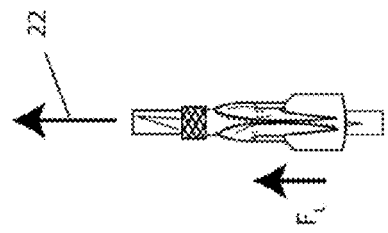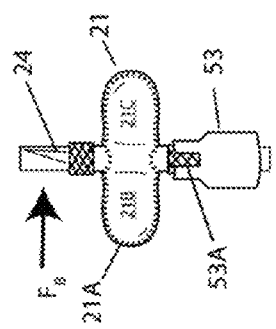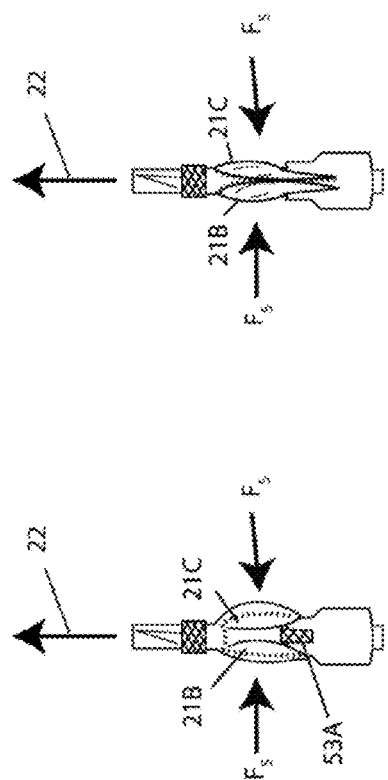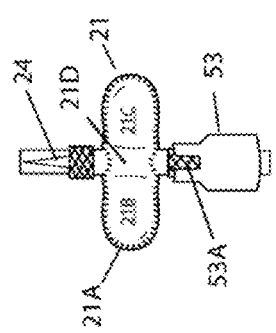

SYSTEMS AND METHODS FOR DELIVERY OF PERITONEAL DIALYSIS (PD) SOLUTIONS

This application is a continuation-in-part of U.S. patent application Ser. No. 11/829,611, filed Jul. 27, 2007, entitled "Systems and Methods for Delivery of Peritoneal Dialysis (PD) Solutions," which is a continuation in part of Ser. No. 11/340,403, filed Jan. 26, 2006, entitled "Systems and Methods for Delivery of Peritoneal Dialysis (PD) Solutions," which is a continuation-in-part of U.S. patent application Ser. No. 11/046,667, entitled "System and Methods for Dextrose Containing Peritoneal Dialysis (PD) Solutions With Neutral PH And Reduced Glucose Degradation Product," filed Jan. 28, 2005, the teachings of all of which applications are incorporated herein by reference.

BACKGROUND OF THE INVENTION

The invention relates to peritoneal dialysis (PD). In particular, it provides containers and methods for treating peritoneal dialysis solutions that reduce glucose degradation products (GDPs).

Peritoneal dialysis (PD) is a medical procedure for removing toxins from the blood that takes advantage of the semipermeable membrane surrounding the walls of the abdomen or peritoneal cavity. During a PD procedure, a solution is introduced into the patient's abdomen, where it remains for up to several hours, removing blood toxins via osmotic transfer through that membrane. At completion of the procedure, the solution is drained from the body along with the toxins.

An active constituent of the PD solution is an osmotic agent, such as glucose, that creates an osmotic gradient across the peritoneal membrane, allowing exchange of toxins from the blood into the peritoneal cavity, as described above. Another constituent is an electrolyte composition, such as a mixture of sodium, calcium, potassium, chlorine, magnesium, and so forth, which restores and maintains electrolyte balance in the blood. A final typical constituent is a buffering agent, such as lactate and pyruvate, which ensures that the blood pH remains at a physiological norms during the procedure.

A major problem with commercially available PD solutions is the presence of degradation products. These products, which typically arise during long-term storage or sterilization of the solutions, damage the peritoneal wall and can adversely affect proteins elsewhere in the patient's body.

Attempts to eliminate these degradation products have met some success. An example is the assignee's own U.S. Pat. No. 6,277,815, which utilizes a multi-chamber PVC or polyolefin bag to separate PD constituents during storage and sterilization. That notwithstanding, there remains a continuing need for improved containers and methods for PD solutions to reduce glucose degradation products (GDPs). That is among the objects of this invention.

Another object of the invention is to provide such containers and methods as can be fabricated at low cost.

Still another object of the invention is to provide such containers and methods as can be fabricated utilizing existing materials and fabrication techniques Still yet still another object of the invention is to provide such containers and methods as can be provided PD solutions of physiologically optimal concentrations and pH levels.

SUMMARY OF THE INVENTION

The foregoing and other objects are attained by the invention which provides, in some aspects, a container system for medical solutions such as peritoneal dialysis (PD) solutions. The invention particularly features a system which includes a first compartment that contains a first medical solution, e.g., a PD osmotic agent, and a second compartment that contains a second medical solution, e.g., a PD buffer agent. The compartments maintain their respective contents separately from one another for purposes of transport, storage and/or sterilization. However, the compartments are fluidly couplable, so that their respective contents can be combined with one another, e.g., following sterilization of the agents and prior to their introduction into the patient's abdomen.

According to some aspects of the invention, the PD buffer agent is highly concentrated and/or highly alkaline. Thus, the buffer agent can be about 3-fold higher in concentration than the chemically "Normal" concentration for that agent, preferably 5-fold or higher, more preferably, 7-fold or higher, more preferably, 10-fold or higher, and still more preferably, 15-fold or higher. Since conventional, commercially-available PD solution buffer agents are of chemically Normal concentrations, the buffer agent according to these aspects of the invention can likewise be about 3-fold higher in concentration than conventional buffer agents, preferably 5-fold or higher, more preferably, 7-fold or higher, more preferably, 10-fold or higher, and still more preferably, 15-fold or higher. Examples of suitable PD buffer agents for use in these aspects of the invention include, but are not limited to, lactate, acetate, and pyruvate. According to related aspects of the invention, the PD buffer agent has a pH of about 8.0 to about 14.0, and, more preferably, a pH of about 9.0 to about 13 and, still more preferably, a pH of about 10.0 to about 12.0.

According to related aspects of the invention, the second compartment (in which that PD buffer agent is stored) has a small volumetric capacity relative to that of the first compartment. Likewise, the volumetric amount of PD buffer agent is small compared to that of the PD osmotic agent. Thus, for example, where the first compartment is of standard clinical use capacity (between 1-5 liters), the second compartment is sized between 5 ml-50 ml, and preferably about 7.5-37.5 ml.

In still other related aspects of the invention, the ratio of the volumetric capacity of the first to second compartments is in the range of about 20:1 to about 200:1, preferably about 50:1 to about 150:1, and preferably about 70:1 to about 140:1, preferably about 90:1 to about 120:1, and most preferably about 133:1.

According to further aspects of the invention, the PD osmotic agent is at physiological use concentrations, i.e., substantially at concentrations at which that agent will be introduced into the patient's abdomen. In related aspects of the invention, those concentrations are between 1.5%-4.25% and, more preferably, between 2.0%-4.0% and, still more preferably, between 2.0%-3.0%.

The PD osmotic agent, moreover, according to related aspects of the invention, is at a physiologically low pH, i.e., a pH below that at which that agent will be introduced into the patient's abdomen. In related aspects of the invention, those pH levels are between 1.0-6.0 and, most preferably, between 1.0-3.0. The PD osmotic agent can be, by way of non-limiting example, a sugar selected from the group consisting of glucose, dextrose, icodextrin, and fructose. In further related aspects of the invention, the first compartment can contain electrolytes, in addition to the osmotic agent.

The first and second compartments are, according to one aspect of the invention, formed in vessels that are fabricated separately from one another. Thus, for example, the first compartment can be formed in a 1-5 liter glass container (e.g., an infusion bottle) or flexible bag (e.g., an infusion bag) made, for example, of PVC, polyolefin, polypropylene, or other medical-grade material) of the type typically used to contain and/or administer peritoneal dialysis fluids. The second compartment can be formed in separate container, such as a tube or vial of flexible, moldable or malleable material such as PVC, all by way of non-limiting example.

In related aspects, the aforementioned vessels adapted so that they can be directly or indirectly physically coupled to one another to support fluid transfer between the compartments. Thus, for example, a PVC bag in which the first compartment is formed can have a port for receiving, by fusing, bonding, interference-fit, screw-fit, or otherwise, a tube in which the first compartment is formed. Alternatively, or in addition, that port can be arranged to receive a needle-like extension, bayonet, or other adapter affixed to such a tube. By way of further example, both vessels can be adapted to receive opposing ends of a common piece of medical-grade tubing.

According to related aspects of the invention, a seal is provided in a fluid-transfer path between the first and second compartments to prevent contact between the PD osmotic agent and the PD buffer agent. The seal is temporary and can be broken, e.g., by a patient, health care provider or manufacturer, to permit the agents to mix following their sterilization and prior to their introduction into the patient's abdomen. The seal may be formed integrally with either of the vessels, e.g., as in the case of a frangible seal formed in the PD buffer-containing vial, or otherwise.

Still further aspects of the invention provide a container system for PD solutions comprising a flexible bag (or glass jar, by way of example) containing a PD osmotic agent and having a standard clinical use capacity, e.g., in the range of 1-5 liters. The system also has a tube containing a PD buffer agent and having a capacity, e.g., in the range of 10-15 mls and/or a pH in the range of 10.0-12.0. The bag and tube are directly or indirectly coupled via respective ports in each of them. A frangible member in the tube prevents mixing of the agents until broken, e.g., by a patient, health care provider or manufacturer, following sterilization of the agents and prior to their introduction into to the abdominal cavity.

Yet still further aspects of the invention provide peritoneal dialysis kits comprising PD osmotic agent-containing and buffering agent-containing vessels as described above. Such kits can also include tubing and other apparatus for coupling the vessels, as well as for introducing the PD solution produced thereby to a patient's abdomen. And, those kits can also include apparatus to facilitate sterilization of the contained osmotic and buffering agents. Moreover, they can include apparatus to facilitate breaking of the above-described frangible (or other sealing) members, e.g., following sterilization of the agents and prior to their introduction into to the abdominal cavity.

Further aspects of the invention provide methods for peritoneal dialysis solutions that contemplate sterilizing a PD osmotic solution contained in a first compartment, sterilizing a PD buffer agent of concentration and/or pH as described above contained in a second compartment, where the first and second compartments are not in fluid communication during the sterilization steps. The method further contemplates placing the first and second compartments in fluid communication following the sterilization step and mixing their contents with one another, prior to introducing the mixed contents into a patient's abdomen.

Still further aspects of the invention provide methods as described above in which the second compartment (in which that PD buffer agent is stored) has a small volumetric capacity relative to that of the first compartment and/or likewise, where the volumetric amount of PD buffer agent is small compared to that of the osmotic agent.

Still further aspects of the invention provide methods as described above that include breaking of a seal between the first and second compartments and, thereby, allowing their contents to mix following the sterilization stage. This can include, for example, bending and/or squeezing a semi-rigid tube that contains the buffer agent (and/or that forms the fluid flow path between the first and second compartments) in order to break a frangible sealing member that separates that agent from the osmotic agent.

Yet still further aspects of the invention provide systems for delivery of PD solutions as described above adapted to ensure mixing of the first and second constituents prior to delivery of the resultant PD solution to the patient. In one such aspect, a system according to the invention comprises a first compartment and a second compartment, e.g., for first and second PD constituents. A first seal prevents fluid transfer between the first compartment and the second compartment, and a second seal prevents fluid transfer between the second compartment and an outlet fluid pathway that leads, e.g., to the patient. Protective structure is provided to deter the patient, his/her health care provider, or others, from breaking the second seal prior to the first seal. This has the benefit, for example, of ensuring expulsion of at least a portion of a PD agent from the second compartment to the first compartment prior to breakage of the second seal.

In a related aspect of the invention, that protective structure is a cover initially positioned in protective relation to the second seal where it inhibits the breaking of that seal. That cover can include an inner passageway and can be slidably disposed to move from the initial position to a second position, where it does not protect the second seal. The size and/or shape of the vessel (or portion thereof) that forms the second compartment restrains such movement—prior to emptying of the second compartment (at least partially) following breaking of the first seal.

In still another aspect of the invention, the second seal is disposed within the vessel that forms the second compartment. Fluid or other pressure from a PD constituent, e.g., a fluid buffer agent, initially contained in that vessel inhibits bending, twisting or other manipulation of it sufficient to break the second seal. Once the first seal has been broken and the PD constituent has been at least partially expelled to the first compartment (for mixing with the other PD constituent), the corresponding reduction of fluid or other pressure in the vessel permits manipulation sufficient to break the second seal.

The first and second compartments, according to other aspects of the invention, comprise separate chambers of a single vessel, e.g., a "multi-chamber" vessel. Thus, for example, those compartments can form separate chambers of a bag, tube or other vessel of flexible, moldable or malleable material such as PVC or other medical grade material. The compartments can be fluidly coupled by a port (e.g., an aperture, tubing or other fluid transfer path) that is, for example, integral to the vessel, affixed to the vessel or otherwise. As above, a temporary and/or breakable seal can be provided in that fluid-transfer path to prevent contact between the fluids (e.g., PD osmotic agent and the PD buffer agent) in the respective containers. That seal may be formed integrally with the pathway, with the vessel or otherwise.

In related aspects, a multi-chambered vessel as described above can be formed to permit at least one of the compartments to be manipulated, e.g., bent, twisted, squeezed and/or folded, at least partially independently of the other. Thus, for example, portions of the vessel in which the respective compartments are formed are at least partially separable from one another so that, for example, one portion can be folded and its respective compartment squeezed without substantially folding the other and squeezing its respective compartment—thus, for example, permitting the user expel liquid from one compartment into the other.

Further related aspects of the invention provide such a multi-chambered vessel as is formed by stamping, cutting, welding, gluing, or otherwise processing one or more sheets or webs of PVC or other suitable material, e.g., to form a bag-like or other-shaped vessel with the aforesaid compartments. A vessel so formed can be perforated in one or more regions between the portions in which the respective compartments are formed. These perforations can be torn by the user to partially separate those portions from one another and to facilitate independent manipulation of their respective compartments (as discussed above); before they are broken, the vessel is more easily handled, e.g., for purposes of manufacture, shipping and handling. In lieu of (or addition to) perforations, the regions can be cut (or otherwise separated) and tacked to the same effect.

Yet still further aspects of the invention provide systems for delivery of PD solutions as described above that include a diffuser in a fluid pathway between the first and second compartments. Such a diffuser can, for example, facilitate homogeneous mixing of the first and second PD agents, even where they are of different viscosities and/or densities.

Related aspects of the invention provide such systems in which the diffuser facilitates such mixing on expulsion of the PD constituent from the second compartment into the first compartment.

Further related aspects of the invention provide such systems in which the diffuser comprises multiple apertures disposed within the first compartment. Those apertures can have diameters, in one aspect of the invention, in the range 1.0 mm-1.5 mm. They can, according to still further aspects of the invention, effect angular dispersion of the PD constituent from the second compartment, upon its expulsion into the first compartment.

Still other aspects of the invention provide systems for delivery of PD solutions as described above in which the vessel (or portion thereof) forming the second compartment folds upon application of force and expels the PD constituent contained therein in connection therewith. A cover that is provided as the aforementioned protective structure comprises a slot or other opening that is sized to slide over at least a portion of the second compartment, depending on a quantity of PD constituent therein.

In related aspects of the invention, the aforementioned slot or other opening is arranged to slide over at least a portion of the vessel forming the second compartment only if that vessel is at least partially folded, in a manner of butterfly wings.

In related aspects of the invention, the aforementioned slot or other opening is arranged to slide over at least the portion of the vessel forming the second compartment only after a quantity of the PD constituent originally contained therein has been expelled therefrom.

In further related aspects of the invention, the slot or other opening is arranged to slide over at least the portion of the vessel forming the second compartment only after at least 10%-30% of a quantity of the PD constituent originally contained in that compartment has been expelled therefrom.

In further related aspects of the invention, the slot or other opening is arranged to slide over at least the portion of the vessel forming the second compartment only after at least 30%-50% of a quantity of the PD constituent originally contained in that compartment has been expelled therefrom.

In further related aspects of the invention, the slot or other opening is arranged to slide over at least the portion of the vessel forming the second compartment only after at least 75% of a quantity of the PD constituent originally contained in that compartment has been expelled therefrom.

Other aspects of the invention provide methods paralleling the operations described above.

Still other aspects of the invention provides container systems and methods as described above for other medical and non-medical solutions.

These and other aspects of the invention are evident in the drawings and in the description that follows.

BRIEF DESCRIPTION OF THE DRAWINGS

A more complete understanding of the invention may be attained by reference to the drawings, in which:

FIGS. 7A-7E illustrate operation of the system of FIG. 6.

FIGS. 11A-11F illustrate configuration and use of the embodiment of FIGS. 8A-8B.

DETAILED DESCRIPTION

Figure 1:
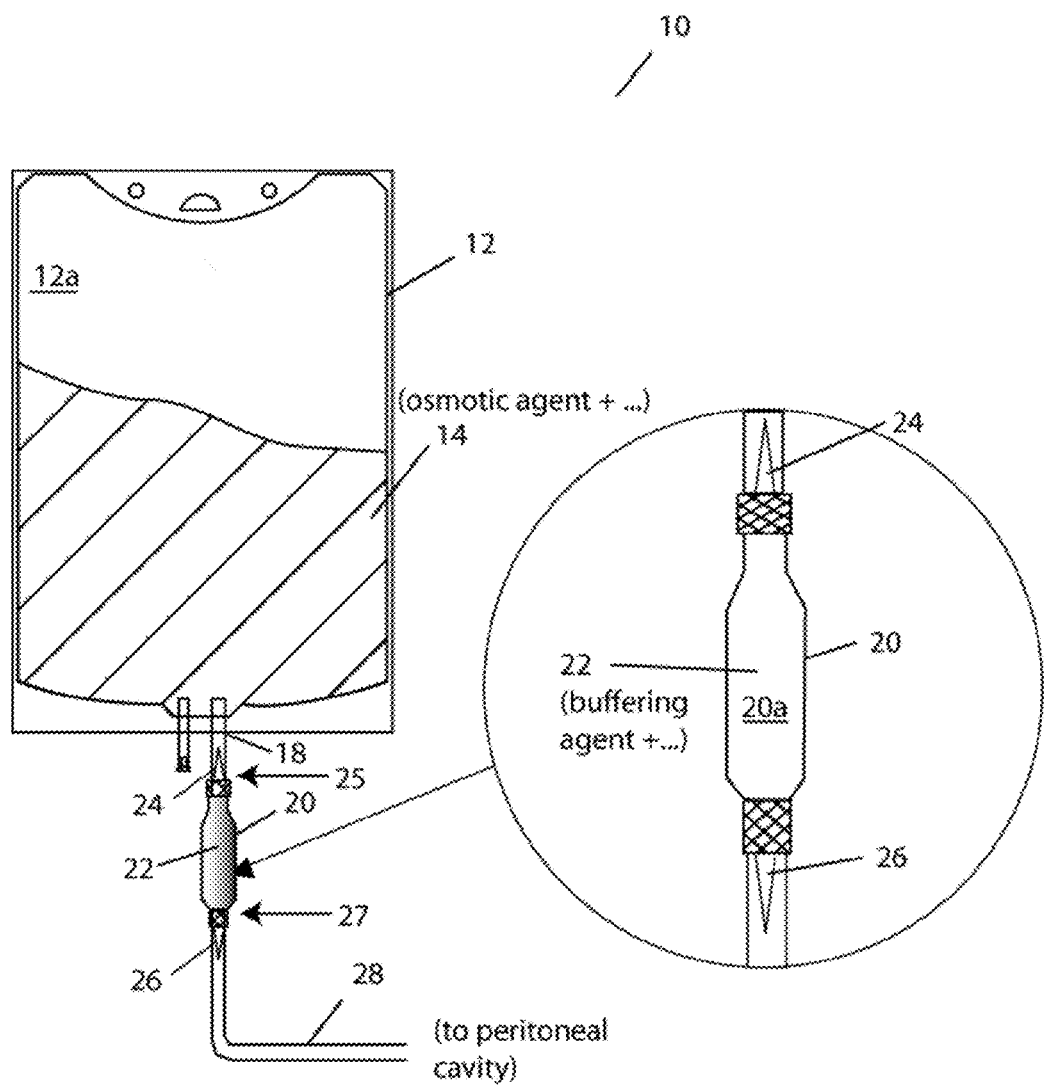
FIG. 1 depicts a system for containing a peritoneal dialysis solution according to one practice of the invention and includes a break-out portion depicting one of the vessels of that system in greater detail.

FIG. 1 illustrates a container system for PD solutions according to one practice of the invention. The container system 10 has a first vessel 12 that contains, in compartment 12a, a PD osmotic agent solution 14. A second vessel 20 contains, in compartment 20a, PD buffer agent solution 22. The vessels 12, 20 and, more particularly, the compartments 12a, 20a are coupled for fluid exchange via port 18 formed in vessel 12, as shown. A temporary seal 24 is provided in the fluid-transfer path between the compartments, also as shown. This prevents contact between or mixing of the PD osmotic agent and the PD buffer agent, e.g., until after sterilization of the agents. A further temporary seal 26 is provided in a catheter 28 that leads, e.g., to the patient's peritoneal cavity (not shown), and prevents flow of PD solution, e.g., until after mixing of the sterilized agents.

Illustrated first vessel 12 is a conventional medical-grade PVC hanging "transfusion" bag, as illustrated. In other embodiments it may be of other configurations and/or comprised of other materials, such as a glass container or other flexible or non-flexible containers (of PVC, polyolefin, polypropylene, or other medical-grade material) of the type typically used to contain and/or administer peritoneal dialysis agents. The compartment 12a is formed within the vessel 12 in the conventional manner and, in the illustrated embodiment, is of standard clinical use capacity (e.g., sized between 1-5 liters), though other sizes may be used as well. As indicated above, vessel 12 includes at least one port 18 providing a fluid-transfer path to compartment 12a. This port can be used to transfer agents to and from the vessel 12, e.g., during manufacture at the pharmaceutical plant, during mixing of the agents, and/or during administration of the mixed agents to the patient. Other embodiments may use a greater or fewer number of ports than those illustrated and, indeed, may use no ports at all (e.g., where needles or other methods are used to add and remove agents from the compartment 12a).

Illustrated vessel 20 is a tube-like vessel (or miniature bulb or "mini-bulb") of PVC or other medical grade material suitable for containing at least a PD buffer agent. The illustrated vessel is semi-rigid and, therefore, suitable for squeezing or other manipulation by a patient, health care provider or manufacturer, e.g., to facilitate breaking of the seal 24, extrusion of the PD buffer agent out from compartment 20a and into compartment 12a, and/or mixing of the PD agents. In other embodiments, the vessel may be of other configurations and may be fabricated from other materials (e.g., rubber, polyolefin, polypropylene, and/or other medical grade materials). Moreover, the vessel need not be semi-rigid: it may be rigid or flexible, depending on how the patient, health care provider or manufacturer are expected to use it for purposes of breaking of seal 24, expelling the PD buffer agent and/or mixing of the PD agents Still further, although vessel 20 has a tube-like configuration, other embodiments may utilize vessels of different shapes. Vessel 20 can be formed by a blow molded or dipping-formed bubble in-line with the solution bag outlet. Other methods for forming the second vessel are possible also, such as formation during the tubing extrusion process (commonly called Bump tubing) or heat forming vessel 20 in pre-extruded tubing.

Illustrated vessel 20 is adapted for direct or indirect coupling with vessel 12 so as to provide a fluid transfer path between compartments 12a, 20a. To this end, vessel 20 has a proximal end port 25 adapted for fusing, bonding, interference-fit, screw-fit or other coupling with vessel 12, hereby, by way of its port 18, as shown in the drawing. In other embodiments, fluidic coupling between the compartments 12a, 20a may be attained in other ways, e.g., by needle- or bayonet-like adapters affixed to either vessel (or its respective port) for receipt by the other vessel.

Vessel 20 is likewise adapted for direct or indirect fluid transfer to the patient's peritoneal cavity. In the illustrated embodiment, this is by way of a distal port 27 adapted for fusing, bonding, interference-fit, screw-fit or other coupling with catheter 28, as shown. That catheter may lead directly to the peritoneal cavity or indirectly, e.g., by way of filters, heaters and/or other medical apparatus.

The compartment 20a of the second vessel 20 has small volumetric capacity in comparison to that of the first vessel 12. Thus, for example, where the first compartment 12a of the illustrated embodiment is of a capacity sized between 1-5 liters, the second compartment 20a is sized about 5-50 ml, preferably about 7.5-37.5 ml. Thus, it will be appreciated that the ratio of volumetric capacity of the first to second compartments is about 20:1 to about 200:1, preferably about 50:1 to about 150:1, and preferably, about 70:1 to about 140:1, and most preferably about 133:1.

Seal 24 is adapted to prevent fluid transfer (or other contact) between the PD agents contained in compartments during manufacture, transport, storage and sterilization of system 10, yet, to permit such fluid transfer upon breaking of that seal 24 (e.g., by a patient, health care provider, or manufacturer) for purposes of mixing the agents following sterilization. In the illustrated embodiment, the patient, health care provider, or manufacturer need not introduce a foreign object (such as a needle) to break the seal 24. Rather, this may be accomplished by squeezing, twisting or other manipulation of vessel 20 and/or port 18. To this end, in the illustrated embodiment, the seal 24 is a frangible member disposed between the aforementioned proximal port of the vessel 20 and the port 18 and is affixed to (and/or formed integrally with) an interior fluid-transfer path of one or both of those ports.

Seal 24 can be fabricated from nylon, plastic, or other medical-grade material, and can be constructed in the manner of conventional frangible seals known in the art and commercially available in the marketplace, e.g., from medical supply manufacturers Baxter, Gambro and Qosina. One preferred seal 24 is constructed in the manner of the frangible seal commercially available from Fresenius Medical Care, e.g., as a component of its Premiere™ Plus Double Bag system. That seal is depicted in FIG. 5.

Referring to the drawing, illustrated seal 24 comprises an elongate member having a head portion 24a and a tail portion 24b, as shown. The latter comprises a main body 24c and flanges 24d which, together, clamp the distal end of port 18 and the proximal end of vessel 20 (as shown), thus, providing physical coupling between the vessels 12 and 20. The tail portion 24b has a central throughway which permits fluid coupling between compartments 12a, 20a, when frangible bond 24e is broken, as discussed below.

The head portion 24a, shown here of generally mushroom cap shape, is coupled to tail portion 24b by frangible bond 24e. Head portion 24a does not include a fluid throughway and, hence, prevents fluid from flowing between compartments 12a, 20a through tail portion 24b so long as bond 24e remains intact. That bond 24e, which may be formed by ultrasonic welding, adhesives, interference fit, fusing, integral molding, or otherwise, breaks upon bending or other manipulation of the seal 24 (e.g., by patient, health care provider, or manufacturer), thereby permitting such flow.

Figure 5:
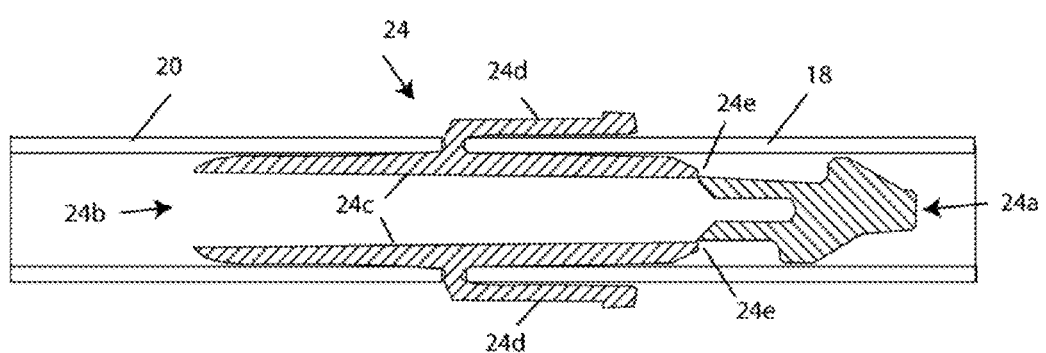
FIG. 5 is a schematic of a frangible seal.

Those skilled in the art will appreciate that FIG. 5 depicts an example of a type of seal which can be used in practice of the invention and that seals of other configurations (frangible or otherwise) which prevent undesired contact between the PD agents, yet, permit such contact to be established by the patient, health care provider, or manufacturer, may be used instead or in addition.

With reference back to FIG. 1, seal 26 is adapted to prevent fluid transfer to the patient prior to both sterilization and mixing of the PD agents. As above, the patient, health care provider, or manufacturer does not need to introduce a foreign object (such as a needle) to break seal 26 but, rather, may be accomplish this by squeezing, twisting or other manipulation of vessel 20, the distal port thereof and/or catheter 28. To this end, as above, the seal 26 of the illustrated embodiment is a frangible member disposed between the aforementioned distal port of the vessel 20 and the catheter and affixed to (and/or formed integrally with) an interior fluid-transfer path of one or both of those. The seal 26, too, can be fabricated from nylon, plastic, or other medical-grade material, and it can be formed in the configurations discussed above in connection with seal 24 (and shown, for example, in FIG. 5).

In the embodiment of FIG. 1, the focus and/or type of manipulation required to break seal 26 differs from that required to break seal 24. This prevents both seals 24, 26 from being unintentionally broken at the same time and, thus, helps insure that the sterilized fluids are mixed prior to their being transferred to the patient. To facilitate this, the seals 24, 26 can be colored differently to alert and remind the user of the proper order in which they are to be broken. Those skilled in the art will appreciate, of course, that coloration can be used in connection with other elements of the system 10, as well.

Figure 6:
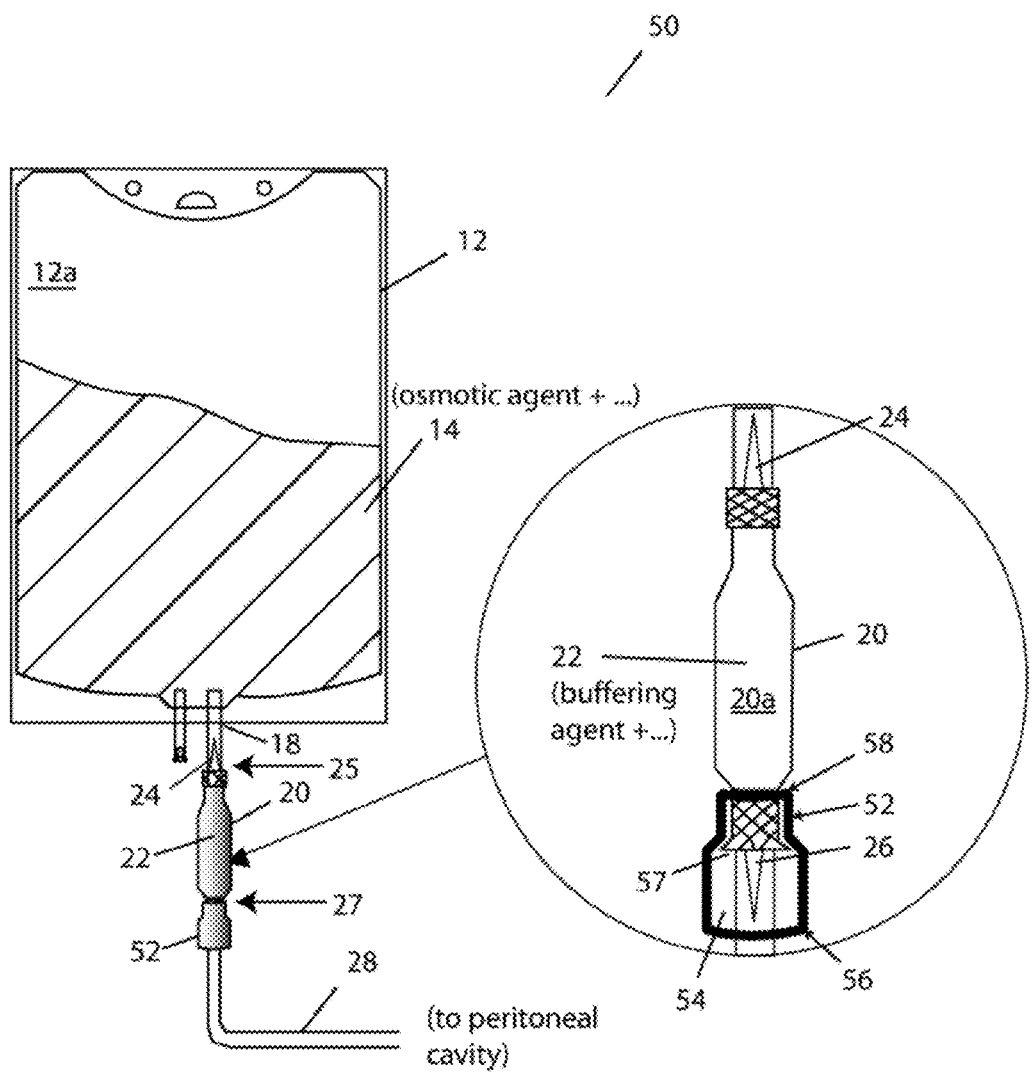
FIG. 6 depicts a system for containing a peritoneal dialysis solution according to one practice of the invention that includes a protective member adapted to inhibit breaking of a second seal prior to breaking of a first seal.

Referring to FIG. 6, additional structure can be provided to further insure that the seals 24, 26 are broken in the proper order and, therefore, to prevent fluid transfer to the catheter 28 (and any downstream equipment) prior to sterilization and mixing of the PD agents. That drawing depicts container system 50 of the same general configuration as container system 10 of FIG. 1 (as indicated by like reference numerals), albeit including a protective member in the form of cover 52 that slides from an initial position, wherein it protects seal 26 from manipulation, to a second position, wherein it permits that seal to be broken. FIGS. 6 and 7A-7C show cover 52 in the initial position. FIG. 7D-7E show the cover 52 in the second position.

Referring to FIG. 6, cover 52 is shown in its initial position, disposed in protective relation to seal 26. In this regard, cover 52 is, more particularly, (a) disposed in surrounding relation to the distal port of vessel 20, the catheter 28 and/or such other structures of system 50 in vicinity of seal 26 that (as discussed above) the patient, health care provider, or other user manipulates in order to break seal 26, and
(b) thereby prevents (or otherwise inhibits) breaking of seal 26 prior to breaking of seal 24.

The cover 52, which can comprise nylon, plastic, or other material (medical-grade or otherwise), preferably, in a rigid or semi-rigid formulation, includes an annular or other internal passageway 54 in which seal 26, the distal port of vessel 20, and/or proximal portion of catheter 28 are initially disposed, as shown in the drawing. The internal passageway extends from a distal end 56 to a proximal end 58 and, in the illustrated embodiment, has an internal diameter that can, though need not, vary therebetween, e.g., as shown.

An inner diameter of the passageway 54, e.g., at the proximal end 58, is sized and shaped to inhibit movement of cover 52 in a distal-to-proximal direction (e.g., "upward" in the drawing) prior to breaking of seal 24, e.g., when vessel 20 contains its post-manufacture complement of PD buffer agent solution 22 (and/or other liquids, gasses or solids). More particularly, the inner diameter of that passageway at the proximal end 58 is smaller than an outer diameter of vessel 20 prior to breaking of seal 24 and any of (a) at least some reduction in that outer diameter (via expulsion of a post-manufacture complement of solution 22 and/or other liquids, gasses or solids) from vessel 20—and, preferably, at least 10%-30% and, still more preferably, at least 30%-50% and, yet still more preferably, at least 50%—of such reduction, and/or (b) a decrease in resistance to such reduction.

The passageway 54 can have a larger inner diameter at the distal end 56 than at the proximal end 58, as shown in the drawing. This can help prevent bending of catheter 28 (e.g., at the point it emerges from end 56) and possible premature breakage of seal 26 during transport, storage and initial use.

Proximal-to-distal movement of cover 52 can also be constrained by a suitable stop—here, for example, a flange 57 at the proximal end of catheter 28 and/or distal end of vessel 20 sized larger than the inner diameter passageway 54 at its proximal end 58 but smaller than the inner diameter of that passageway at its distal end 56. As shown in the drawing, the flange permits distal-to-proximal movement of the cover 52, but inhibits its proximal-to-distal movement.

In some embodiments of the invention, the cover 52, as well as the seals 24, 26, are colored differently to alert and remind the user of the proper order in which they are to be broken. Those skilled in the art will appreciate, of course, that coloration can be used in connection with other elements of the system 10, as well.

FIGS. 7A-7E depict use of cover 52—initially protecting, then, permitting manipulation (and breaking) of seal 26.

Initially, as shown in FIG. 7A, seals 24, 26 are unbroken and compartment 20a contains its post-manufacture complement of buffer agent 22 (and/or other gasses, fluids, solids). Consistent with the discussion above, with the compartment 20 in this condition, the size differential between outer diameter of vessel 20 and inner diameter of passageway 54 inhibits distal-to-proximal (e.g., "upward") movement of cover 52.

Referring to FIGS. 7B-7C, the cover 52 remains in its initial position while the user breaks seal 24 (e.g., by bending the proximal end of vessel 20 relative to port 18) and compresses vessel 20 in order to expel buffer agent 22 for mixing with osmotic agent 14.

Referring to FIG. 7D, the user slides the cover in the distal-to-proximal direction over the vessel 20 and away from the seal 26, once the seal 24 has been broken and the outer diameter of vessel 20 has been reduced (or, at least, resistance to such reduction has been eliminated). With the cover 52 moved, the user can more readily manipulate the distal end of vessel 20 and/or the proximal end of catheter 28 in order to break seal 26. See FIG. 7E.

Those skilled in the art will appreciate that cover 52 and/or vessel 20 can have shapes other than those shown in FIGS. 6 and 7, yet, operate in the manner discussed above in connection therewith.

Figure 8A:
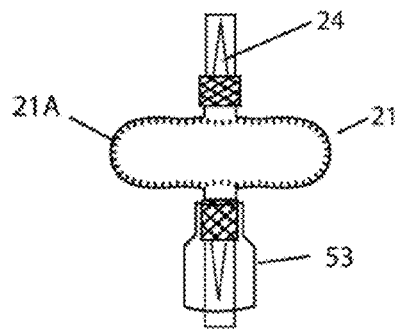
FIGS. 8A-8B illustrate an embodiment of the invention incorporating an alternate configuration of the second container of FIG. 6.
Figure 8B:
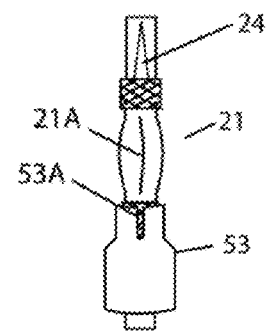

One such alternate configuration is depicted in FIGS. 8A-8B, which shows in front- and side-views, respectively, a vessel 21 having the same function as element 20, above—albeit shaped with a central portion that is elongate in the transverse direction and that generally defines an oval shape, as shown. The vessel 21 of the illustrated embodiment is formed from halves (or other portions) of PVC, polyolefin or other medical-grade flexible or semi-rigid material that are glued, ultrasonically welded or otherwise fused along an edge 21A in the conventional manner known in the art (although the vessel can be formed—from a single portion or multiple portions—in other ways).

The cover 53 of FIGS. 8A-8B functions in the same manner as cover 52, above, albeit it includes a slot 53A that skirts the edge 21A when the cover 53 is slid in the distal-to-proximal direction over the vessel 21 and away from the seal 26 (once the seal 24 has been broken and the volume of vessel 21 has been reduced).

In comparison to the configuration of FIGS. 6-7, that shown in FIGS. 8A-8B requires more complete reduction in outer diameter (via expulsion of a post-manufacture complement of solution 22 and/or other liquids, gasses or solids) from vessel 21 in order to permit distal-to-proximal movement of cover 53.

FIGS. 11A-11F depict a configuration and use of vessel 21 to facilitate expulsion of the post-manufacture complement of solution 22 (and/or other liquids, gasses or solids) into vessel 12 (not shown in these drawings) for mixing with solution 14 prior to introduction of the resulting solution into the patient's abdomen. Such expulsion is graphically depicted in FIGS. 11C-11F by the arrow labeled 22. As with vessel 21 of FIGS. 8A-8B, vessel 21 of FIGS. 11A-11F serves a same function as vessel 20, described earlier, and may be used (e.g., preferably, along with cover 53) in place of vessel 20 (or alternates therefore, e.g., vessel 42, discussed elsewhere herein) in systems according to the invention.

As above, the vessel 21 of FIGS. 11A-11F has a central portion that is elongate in the transverse direction and that generally defines an oval shape. And, as above, it is formed from halves (or other portions) of PVC, polyolefin or other medical-grade flexible or semi-rigid material that are glued, ultrasonically welded or otherwise fused along an edge 21A in the conventional manner known in the art (although the vessel can be formed—from a single portion or multiple portions—in other ways).

Preferably, the vessel 21 of FIGS. 11A-11F is formed to facilitate folding of its halves 21B, 21C when the vessel is squeezed, e.g., by the patient, health care provider or otherwise, following breakage of seal 24. This is graphically depicted in steps 11B showing breaking of the seal 24 (as indicated by force arrows $F_B$), and 11C-11E showing folding of the halves 21B, 21C when squeezed (as indicated by force arrows $F_S$).

Such folding can be facilitated, by way of non-limiting example, by pre-creasing vessel 21 in a central region 21D, by reducing a cross-section of the vessel 21 in that region 21D, or otherwise. Indeed, in the illustrated embodiment, such folding is facilitated, at least in part, by the proximal and distal ports of the vessel 21, the affixation of which in vicinity of region 21D provide an axis about which halves 21B, 21C tend to naturally bend.

The cover 53 of FIGS. 11A-11F functions in the same manner as cover 53 of FIGS. 8A-8B. Albeit, slot 53A of the cover of FIGS. 11A-11F is positioned, sized and shaped to inhibit movement of the cover in a distal-to-proximal direction prior to breaking of seal 24 and expulsion from vessel 21 of a post-manufacture complement of PD buffer agent solution 22 (and/or other liquids, gasses or solids). More particularly, the slot is positioned so that it (and, consequently, cover 53 itself) cannot be slid in the distal-to-proximal direction until both sides 21B, 21C are aligned with the slot. Since only one such slot is provided in the illustrated embodiment—generally, aligned normal to the plane of the vessel 21 (as shown in the drawings)—this necessitates squeezing the sides 21B, 21C together (in the manner of butterfly wings) or otherwise folding the vessel 21 at least partially and, preferably, substantially.

Moreover, the slot 53A is sized and shaped to prevent such sliding until a cross-section of the region of sides 21B, 21C over which it (slot 53A) slides is reduced, i.e., via squeezing and expulsion of solution 22 (and/or other liquids, gasses or solids) from vessel 21—preferably, by at least 10%-30% volumetrically and, still more preferably, at least 30%-50% volumetrically and, yet still more preferably, at least 75% volumetrically and, yet, still more preferably, substantially all of that solution. This is graphically depicted in step 11F, showing repositioning of the cover 53 via a sliding force, as indicated by arrow $F_L$. As evident in the drawing, the cover 53 of the illustrated embodiment does not cover the entire vessel 21 when repositioned but, rather, only the central portion: the outer "wings" of sides 21B, 21C remain outside. Of course, other embodiments may vary in this regard.

In some embodiments, slot 53A has rails, flats or other structures that effect further squeezing of the halves 21B, 21C and consequent expulsion of solution 22 (and/or other liquids, gasses or solids) therefrom when that cover is slid in the distal-to-proximal direction over those halves.

The internal passageway of the cover 53 of FIGS. 11A-11F (like passageway 54, discussed above) can be sized analogously to slot 53A, i.e., to inhibit movement of the cover in a distal-to-proximal direction prior to breaking of seal 24 and reduction in that an outer diameter of a central region of vessel 21 via squeezing and expulsion of a post-manufacture complement of solution 22 (and/or other liquids, gasses or solids) from vessel 21. And, as discussed earlier, the internal passageway of the cover 53 of FIGS. 11A-11F can have a larger inner diameter at the distal end than at the proximal end, e.g., to help prevent bending of catheter 28 and possible premature breakage of seal 26. And, as above, proximal-to-distal movement of that cover 53 can be constrained by a suitable stop and/or relative sizing of the inner diameter of the internal passageway of the cover.

Of course, those skilled in the art will appreciate that the slot (or other opening) 53A and inner passageway of cover 53 of FIGS. 11A-11F can be aligned, shaped and sized otherwise (and, indeed, that multiple slots could be provided on cover 53A) in accord with the teachings hereof.

In some embodiments, the seal 24, the vessel 21, and the cover 53 are colored differently to alert and remind the user of the proper order in which they are to be utilized. Thus, for example, the seal 24 can be colored red; the cover 53 can be colored white; and, the seal 26 can be colored blue. This red-white-blue combination can be effective in reminding patients or health care providers in locales where those colors have memorable significance (e.g., in the United States or France) that the seal 24 (red) is to be broken, first; the cover 53 (white) is to be slid, next (after squeezing out the contents of vessel 21); and, that the seal 26 (blue) is to be broken, last. Of course other color combinations or visual indicia (e.g., lettering, numbering or other symbology) may be used instead or in addition in other locales and/or among other patients or health care provider.

Preferably, the vessel 21 of FIGS. 11A-11F is formed to facilitate folding of its halves 21B, 21C when the vessel is squeezed, e.g., by the patient, health care provider or otherwise, following breakage of seal 24. This is graphically depicted in steps 11B showing breaking of the seal 24 (as indicated by force arrows $F_B$), and 11C-11E showing folding of the halves 21B, 21C when squeezed (as indicated by force arrows $F_S$).

Referring now to FIGS. 15 and 16A-16F, there is shown an alternate arrangement of the container system of FIGS. 1 and 11A-11F, here, with the PD agent-containing compartments 12a, 20a formed in a single vessel, e.g., a dual compartment bag or, more generally, a multi-chamber vessel. Such a container system is advantageous, for example, insofar as it facilitates handling during manufacture and shipping, yet, affords the patient, health care provider or other user the other benefits of the systems described herein. An understanding of the embodiment of FIGS. 15, 16A-16F may be appreciated by study of that drawing and the text that follows in view of the discussion elsewhere herein. In these drawings, use of reference numerals like those referred to previously (or elsewhere herein) indicates like structure and functionality, albeit as adapted for use with the embodiment of that drawing.

Figure 15:
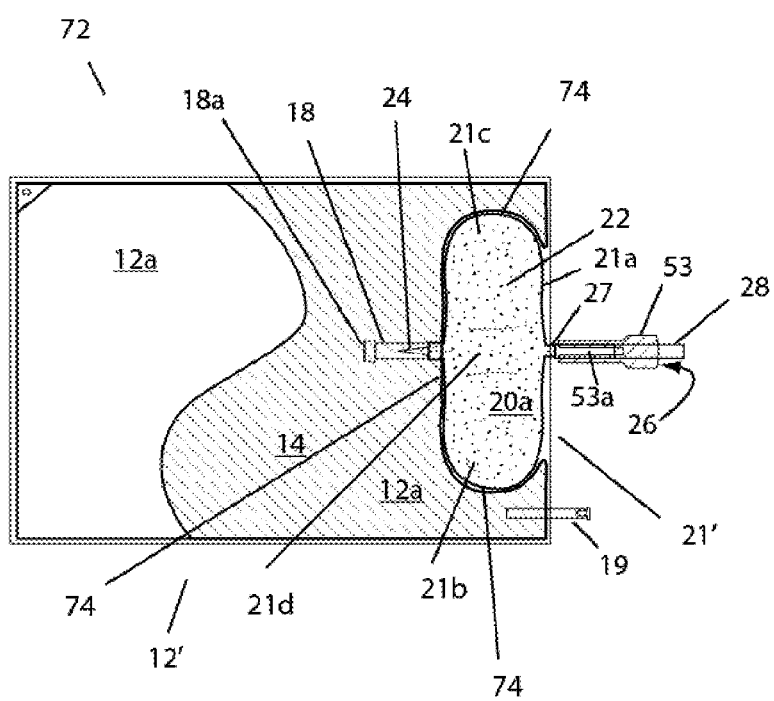
FIG. 15 depicts a multi-chamber vessel for containing a peritoneal dialysis solution according to one practice of the invention.

The container 72 shown FIG. 15 includes two portions: one (labelled 12') that embodies the overall structure and functionality of vessel 12 and that includes compartment 12*a* for PD osmotic agent solution 14; the other (labelled 21'), that embodies the overall structure and functionality of vessel 21 and that includes compartment 20*a* for PD buffer agent solution 22. In practice, vessels 12 and 21 as discussed above can be fabricated separately and assembled together to form a single vessel 72 (e.g., in a configuration as shown in FIG. 15) with compartments 12*a*, 20*a*. Thus, for example, vessel 21 can be shaped with a central portion that is elongate in the transverse direction (or otherwise), as shown, and vessel 21 can be generally rectangular (or otherwise), as shown, with a "cut-out" to fit, mate with, or otherwise accommodate vessel 12, e.g., as shown. Preferably, however, vessel 72 is directly formed (e.g., from sheets or webs of PVC or other suitable material) to incorporate portions 12' and 21' and their respective chambers 12*a* and 20*a*, as well as one or more of the additional elements shown in the drawing and/or discussed below. Such fabrication is detailed in the sections that follow.

Illustrated vessel 72 can be fabricated from medical-grade PVC, e.g., in the manner of a hanging "transfusion" bag, as illustrated, though it may be of other configurations and/or comprised of other materials, such as flexible polyolefin or other medical-grade materials suitable used to contain and/or administer peritoneal dialysis agents. The illustrated embodiment is sized for large capacity, e.g., delivery of 6 liters or above of PD solution, though, it can be sized for standard clinical use capacities (e.g., sized between 1-5 liters) as well. The compartments 12*a*, 20*a* are proportioned as discussed above, i.e., such that compartment 20*a* is of small volumetric capacity in comparison to that compartment 12*a*. Thus, for example, where the first compartment 12*a* of the illustrated embodiment is of a capacity sized between 1-5 (or 6) liters, the second compartment 20*a* is sized about 5-50 ml (or 60 ml), preferably about 7.5-37.5 ml (or 45 ml). Thus, it will be appreciated that the ratio of volumetric capacity of the first to second compartments is about 20:1 to about 200:1, preferably about 50:1 to about 150:1, and preferably, about 70:1 to about 140:1, and most preferably about 133:1. Of course, it will be appreciated that the vessel and its respective compartments 12*a*, 20*a* can be sized otherwise for delivery of even larger and smaller amounts of PD solution.

The compartments 12*a*, 20*a* are coupled for fluid exchange via port 18 (e.g., an aperture or tubing) that defines a fluid transfer path. In the embodiment of FIG. 15, the port 18 is disposed internally to one or more of the compartments 12*a*, 20*a*—here, compartment 12*a*, as shown. The port 18 can be formed integrally with vessel 72 and/or one of its constituent portions 12' and 21'. Alternatively, or in addition, coupling between that port and the vessel (and/or portions 12', 21') can be provided via fusing, bonding, interference-fit, screw-fit or other coupling mechanisms. As above, fluidic coupling between the compartments 12*a*, 20*a* may be attained in other ways, e.g., by needle- or bayonet-like adapters affixed to either vessel (or its respective port) for receipt by the other vessel. Regardless, the port 18 (or other fluidic coupling) can incorporate a diffuser 18A as discussed below, e.g., in connection with FIGS. 12A-12E.

Illustrated vessel 72 includes additional ports, as well. Thus, it includes port 19, which can be used to transfer agents to and from the compartment 12*a*, e.g., during manufacture at the pharmaceutical plant, during mixing of the agents, and/or during administration of the mixed agents to the patient. It also includes port 27, disposed as shown, that provides a direct fluid outlet from chamber 20*a* and that is coupled to catheter 28 at a junction which is obscured in the drawing by cover 53. Such coupling can be provided by fusing, bonding, interference-fit, screw-fit or other mechanisms known in the art. Other embodiments may use a greater or fewer number of ports than those illustrated and, indeed, may use no ports at all (e.g., where needles or other methods are used to add and remove agents from the compartment 12*a*).

As above, a temporary seal 24 is provided in the fluid-transfer path defined by port 18. This prevents contact between or mixing of the PD osmotic agent and the PD buffer agent, e.g., until after sterilization of the agents. Also as above (see, for example, FIGS. 11A-11F and the accompanying text), a further temporary seal 26 (here, obscured by cover 53) is provided in catheter 28 that leads, e.g., to the patient's peritoneal cavity (not shown), and prevents flow of PD solution, e.g., until after mixing of the sterilized agents. The seals 24, 26 may be constructed and fabricated as discussed above, for example, in connection with FIGS. 1 and 5. In some embodiments, catheter 28 includes a connector for downstream apparatus, such as a PD tubing set, a peritoneal infusion port, or otherwise. One preferred such connector is the Safe-Lock Connector™ commercially available from the assignee hereof. In embodiments utilizing that connector, or the like, the seal 26 may comprise a frangible element integral thereto.

As with the embodiment discussed in connection with FIGS. 11A-11F, cover 53 is slotted, and it slides from an initial (distal) position, wherein it protects seal 26 from manipulation, to a second (proximal) position, wherein it permits that seal to be broken. In the embodiment of FIG. 15, the slot 53A skirts over edge 21A of the portion 21' that forms the second chamber 20*a*, when the cover 53 is slid in the distal-to-proximal direction over that portion of vessel 72 and away from the seal 26 (once the seal 24 has been broken and the volume of vessel 21 has been reduced). Cover 53 and slot 53*a* are sized and positioned to require that a specified volume of solution 22 and/or other liquids, gasses or solids be expelled from cavity 20A and its outer diameter be correspondingly reduced in order to permit distal-to-proximal movement of cover 53.

Figure 16A:
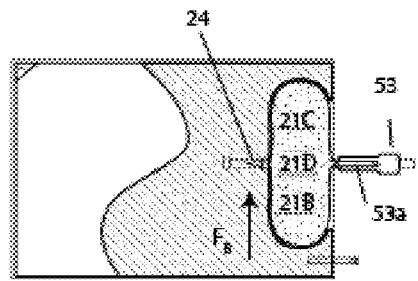
FIGS. 16A-16F depicts a manner of use of the multi-chamber vessel of FIG. 15.
Figure 16D:
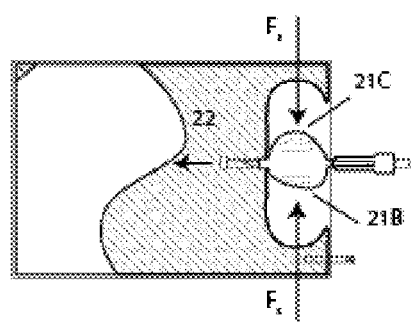
Figure 16B:
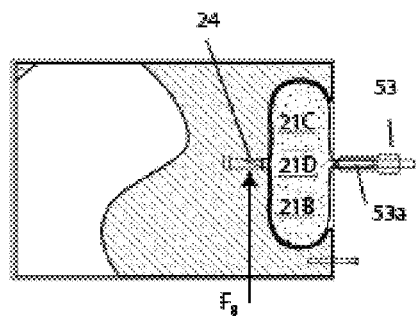
Figure 16E:
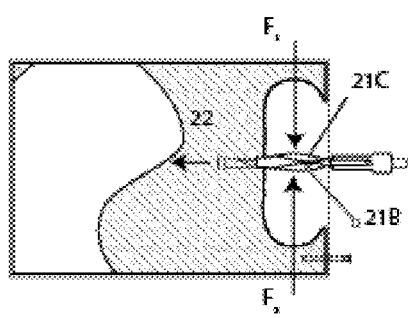
Figure 16C:
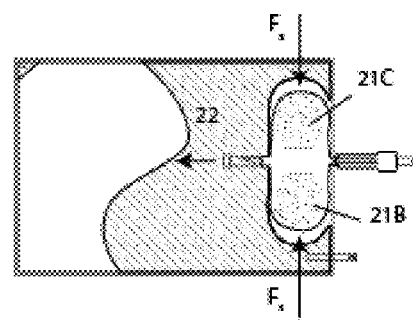
Figure 16F:
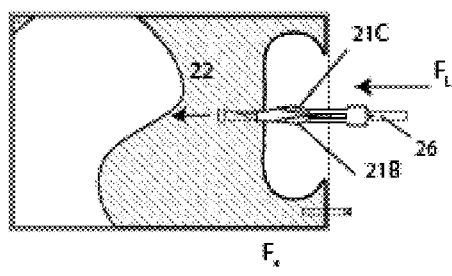

In this regard, portion 21' of illustrated vessel 72 is formed to facilitate folding of halves 21B, 21C of portion 21' when it is squeezed, e.g., by the patient, health care provider or other user, following breakage of seal 24. This is graphically depicted in FIG. 16B showing breaking of the seal 24 (as indicated by force arrows FB), and 16C-16E showing folding of the halves 21B, 21C when squeezed (as indicated by force arrows FS).

As above, such folding can be facilitated, by way of non-limiting example, by pre-creasing portion 21' in a central region 21D, by reducing a cross-section of the portion 21' in that region 21D, or otherwise. Indeed, in the illustrated embodiment, such folding is facilitated, at least in part, by the ports 18, 27, the affixation of which in vicinity of region 21D provide an axis about which halves 21B, 21C tend to naturally bend.

The cover 53 of the embodiment shown in FIGS. 15, 16A-16E functions in the same manner as cover 53 of FIGS. 11A-11F. Thus, for example, slot 53A of the cover of FIGS. 15, 16A-16E cannot be slid in the distal-to-proximal direction until both sides 21B, 21C are aligned with the slot. Since only one such slot is provided in the illustrated embodiment—generally, aligned normal to the plane of the portion 21' (as shown in the drawings)—this necessitates squeezing the sides 21B, 21C together (in the manner of butterfly wings) or otherwise folding the vessel 21 at least partially and, preferably, substantially.

As noted above, in some embodiments vessel 72 is directly fabricated with portions 12' and 21' and their respective chambers 12a and 20a. By way of example, the vessel 72 can be fabricated from two layers (or a single folded layer) of PVC, flexible polyolefin or other suitable sheet or web material that is cut, formed and ultrasonically welded, glued or otherwise assembled to form a vessel of the configuration shown in FIGS. 15 and 16A-16F. Ports 18 (including diffuser 18) and 27 can be fashioned simultaneously and/or incorporated into the vessel during such assembly.

In the illustrated embodiment, the vessel 72 is fabricated such that portions 12' and 21' are attached to one another (or substantially so) for purposes of manufacture and shipping, yet, can be partially separated from one another, e.g., by the patient, health care provider or other use prior to mixing of the PD solution. Such partial separation permits at least one of the compartments 12a, 20a and, preferably, compartment 20a, to be manipulated, e.g., bent, twisted, squeezed and/or folded, at least partially independently of the other compartment 12a, e.g., in the manner shown in FIGS. 16B-16F. Thus, for example, as shown in those drawings, portion 21' can be separated from portion 12' so that, for example, it can be squeezed, folded and the contents 22 of its respective compartment 20a expelled into compartment 12a without substantially folding portion 12' and squeezing its respective compartment 12a.

To this end, during fabrication of vessel 72, the PVC, flexible polyolefin or other fabrication material is perforated in one or more regions 74 between the portions 12', 21. Prior to use, those perforations can be torn by the patient, health care provider to partially separate those portions from one another—and, more specifically, for example, to permit separation of the type shown in FIGS. 16B-16F—and to facilitate independent manipulation of their respective compartments as also shown there. In lieu of (or addition to) perforations, the portions can be cut (or otherwise separated) from one another in the region(s) 74 and tacked ultrasonically, or otherwise, to like affect. By leaving the perforations or tack-welds unbroken until use, processing and handling of the vessel 72 is facilitate during manufacture and shipping.

FIGS. 12A-12E depict a container system 10 in which port 18 of vessel 12 includes a diffuser 18A for facilitating mixing of solution 22 (and/or other liquids, gasses or solids of vessel 21) with solution 14 (of vessel 12). The diffuser 18A is shown in use with a system 10 that includes a vessel 12 of the type shown in FIGS. 1, 3, 4, 6, 9, and a vessel 21 and cover 53 of the types disclosed in FIGS. 11A-11F; however, it will be appreciated that it the diffuser 18A can be utilized in connection with the other vessels and/or configurations shown and/or discussed herein.

Figure 12A:
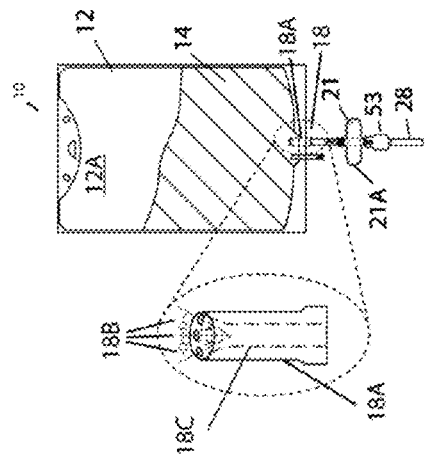
FIGS. 12A-12E depict use of a container system according to the invention that includes a diffuser in a fluid pathway between the vessels.
Figure 12B:
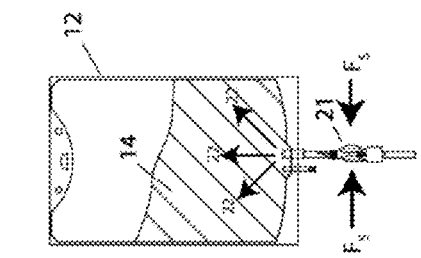
Figure 12D:
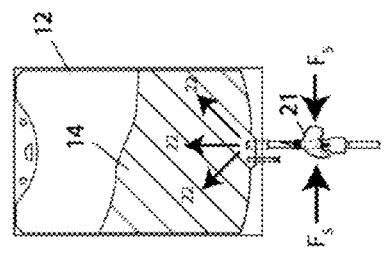
Figure 12C:
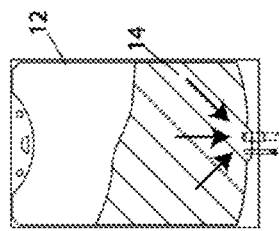
Figure 12E:
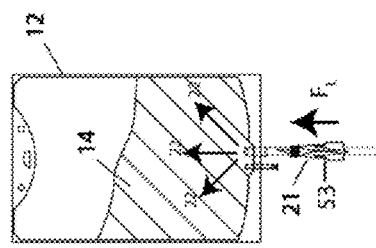

Referring to FIG. 12A, the diffuser 18A of the illustrated embodiment comprises a cap—here, of a generally elongated shape, but of other shapes in other embodiments—having a proximal end that is disposed within compartment 12A and that includes multiple inlet/outlet apertures 18B. A distal end of the diffuser cap is coupled to and/or comprises tubing (or other structure) defining port 18, which, as noted above, provides for fluid coupling between the vessels 12 and 21.

Three such apertures 18B are shown on the proximal end of the illustrated diffuser 18A, though, other pluralities of apertures may be used in other embodiments, e.g., two apertures, four apertures, five apertures, and so forth. And, while apertures 18B are disposed in the illustrated embodiment at the tip of the proximal end of the diffuser 18A, in other embodiments they may be disposed elsewhere on diffuser 18A in fluid communication with compartment 12A Illustrated apertures 18B are in fluid communication with an internal channel 18C that extends to the distal end of diffuser 18A and that supports fluid coupling between vessels 12, 21, as shown. In the illustrated embodiment, two of the three apertures 18B extend from the channel 18C at an angle $\Omega$, while one of the apertures is in line with the channel 18C, all as shown. As a result, diffuser 18A of the illustrated embodiment causes solution 22 that is expelled into vessel 12 to disperse with an angular dispersion of $2\Omega$ into solution 14, though the diffuser of other embodiments may effect other angular dispersions.

The angle $\Omega$ of the illustrated embodiment is in the range 20°-70° (with a resulting angular dispersion $2\Omega$ in the range 40°-140°) and, more preferably 30°-60° (with a resulting angular dispersion $2\Omega$ in the range 60°-120°) and, still more preferably, about 25° (with a resulting angular dispersion $2\Omega$ of about 50°), as shown. In other embodiments, other angular ranges may be used depending on the location of the proximal tip of diffuser 18A within compartment 12A, the size of that compartment, the characteristics of the fluids being mixed, and so forth. Although the apertures are disposed symmetrically about an axis in the illustrated embodiment, other embodiments may forego such symmetry.

Diffuser 18A may comprises nylon, plastic, or other medical-grade material (and, preferably, such medical materials as do not fuse to PVC during heat sterilization). In the illustrated embodiment, diffuser 18A is fabricated from polycarbonate and is the same material as used in frangible members (e.g., 62, 64) discussed elsewhere herein. In other embodiments, diffuser 18A is fabricated from polyvinylchloride (PVC) and is the same material as used for the catheter 28 and other ports and/or tubing that comprise system 10. The apertures 18C of the illustrated embodiment are preferably 1.0 to 1.5 mm in diameter, though other embodiments may use apertures of different and/or varying sizes, e.g., depending on the characteristics of the fluids being mixed and other factors indicated above, all by way of example.

Diffuser 18A facilitates mixing of solution 22 (and/or other liquids, gasses or solids in vessel 21) with solution 14 when the patient or health care provider squeezes vessel 21 in the manner shown in FIGS. 11C-11F. This is graphically depicted in steps 12B-12D showing expulsion of fluid 22 (as indicated by arrows 22) when container 21 is squeezed (as indicated by force arrows $F_S$) and cover 53 is slid (as indicated by force arrow $F_L$).

Diffuser 18A further facilitates mixing of those solutions, following breakage of seal 26, when the combined PD solution is expelled into the catheter 28 (and any downstream equipment) for introduction to a patient. This is graphically depicted in step 12E showing expulsion (e.g., under the force of gravity and/or manipulation of vessel 12) of the combined solutions 14, 22 from the vessels 12 and 21, and exit via the catheter 28 (all as indicated by the unlabelled arrows).

The configurations shown in FIGS. 11A-11F and 12A-12E may be used in connection with the PD osmotic agents, PD buffer solutions and other PD components discussed below. In this regard, it will be appreciated that, consistent with the remarks above, vessel 21 may be used (e.g., along with cover 53 or alternates therefor) in place of vessel 20 (or alternates therefor, e.g., vessel 42) discussed below and elsewhere herein.

Advantages of the configurations shown in FIGS. 11A-11F and 12A-12E include that they permit the solutions 14 and 22 to be more readily combined following expulsion of solution 22 into vessel 12, e.g., necessitating limited manipulation by the patient or health care provider in order to assure an acceptable mix of PD solution that lacks pH extremes and is an appropriate range for introduction to the patient. In this regard, for example, the diffuser 18A facilitates mixing PD solutions of different densities and/or viscosities—and, particularly, by way of non-limiting example, a PD buffer solution 22 that has density and/or viscosity greater than that of the PD osmotic agent 14—to be mixed quickly and homogeneously, with minimal effort. An advantage of the vessel 21 of FIG. 11A is that squeezable folding of its sides 21B, 21C (as detailed above) increases infusion pressure of solution 22 for better mixing in vessel 12. It also better increases chances for complete infusion of solution 22.

In this context a procedure for use of system 10 as shown in FIGS. 12A-12E is shown in FIGS. 13A-13F. The system of FIGS. 13A-13F, additionally includes a drain bag 23, which can be supplied with the system 10 for use in draining spent PD solution from the patient.

Figure 13A:
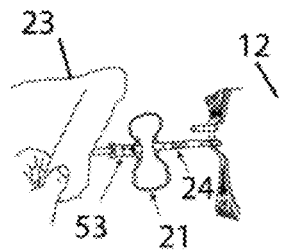
FIGS. 13A-13F depict a procedure for use of the container system depicted in FIGS. 12A-12E.

Referring to FIG. 13A, prior to use of the system 10, the patient or health care provider inspects and familiarizes himself/herself with vessels 12, 21, seals 24, 26 and cover 53.

Figure 13B:
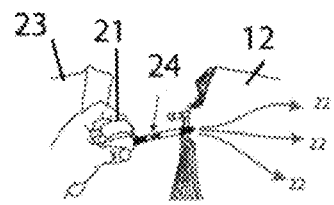

Referring to FIG. 13B, the patient or health care provider next breaks the seal 24 (which, as noted above, can be differentially colored red or otherwise in some embodiments) and, then, folds the vessel 21 in half, squeezing firmly until the solution 22 originally contained in the vessel 21 is expelled into solution 14 of vessel 12.

Figure 13C:

Referring to FIG. 13C, the patient or health care provider next presses on vessel 12 in order to push solution back into vessel 21. In some embodiments, the steps shown in FIGS. 13B and 13C are carried out three times to facilitate thoroughly "washing" solution 22 from vessel 21.

Figure 13D:
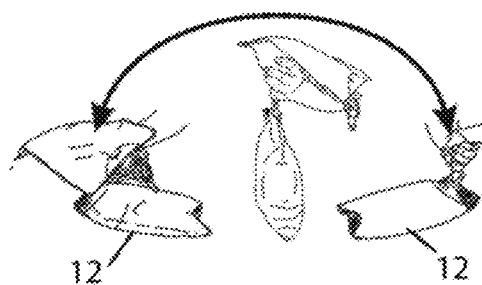

Referring to FIG. 13D, the patient or health care provider next inverts the system 10 (and, significantly, vessel 12) to facilitate still more thorough mixing of the solutions 22, 44. In some embodiments, the step shown in FIG. 13D is carried out three times to facilitate thorough mixing of the solutions 14, 22.

Figure 13E:
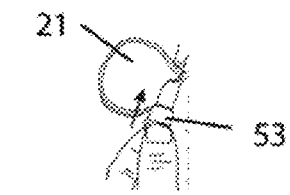

Referring to FIG. 13E, the patient or health care provider next folds vessel 21 in half and slides the cover 53 (which, as noted above, can be differentially colored white or otherwise in some embodiments) up over the central portion of the vessel 21 until the seal 26 (which, as noted above, can be differentially colored blue or otherwise in some embodiments) is exposed where the tubing comprising catheter 28 is attached.

Figure 13F:
Figure 14A:
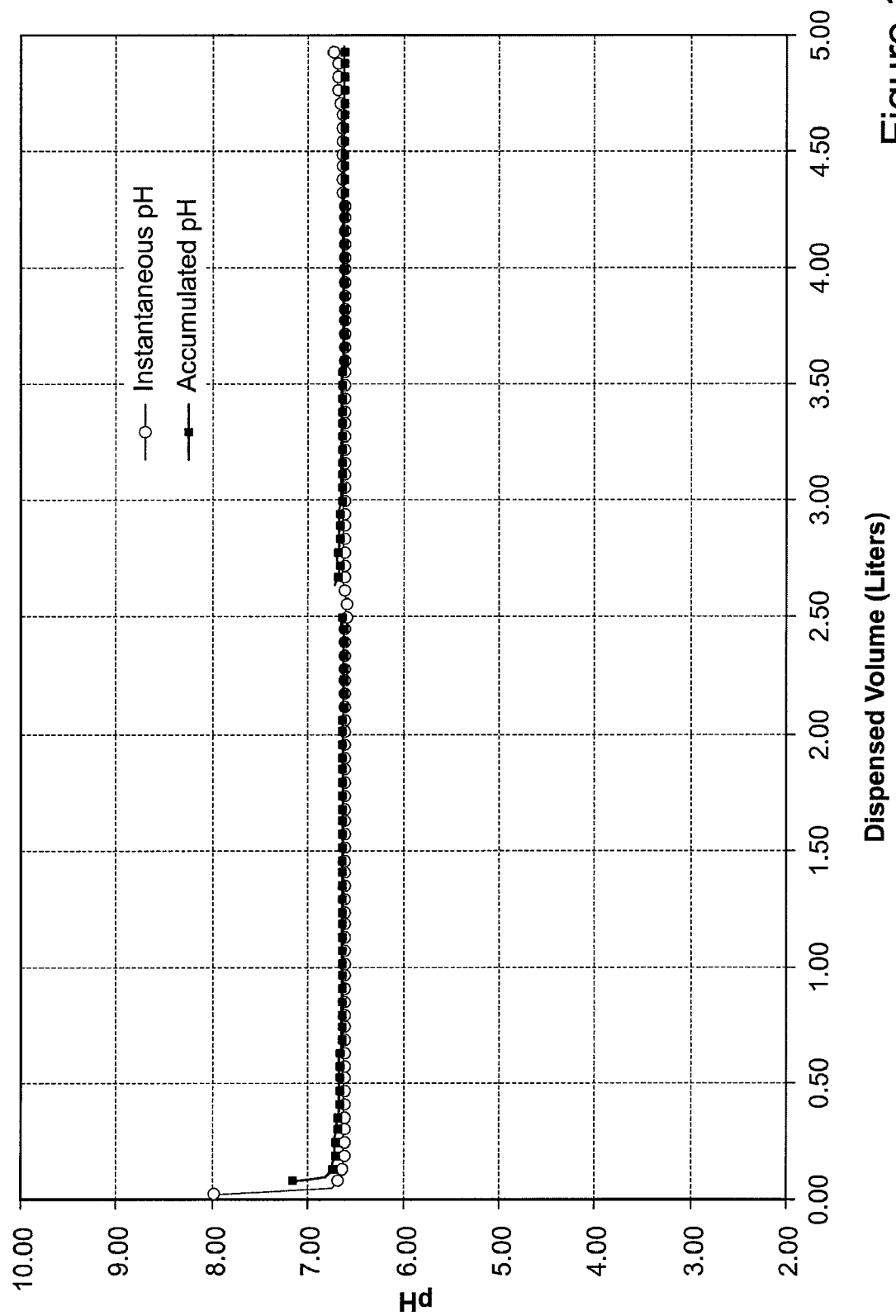
FIGS. 14A-14E are graphs of pH as a function of the outflow volume of the catheter of sample systems of the type shown in FIGS. 12A-12E when used with normally expected operating procedures.
Figure 14B:
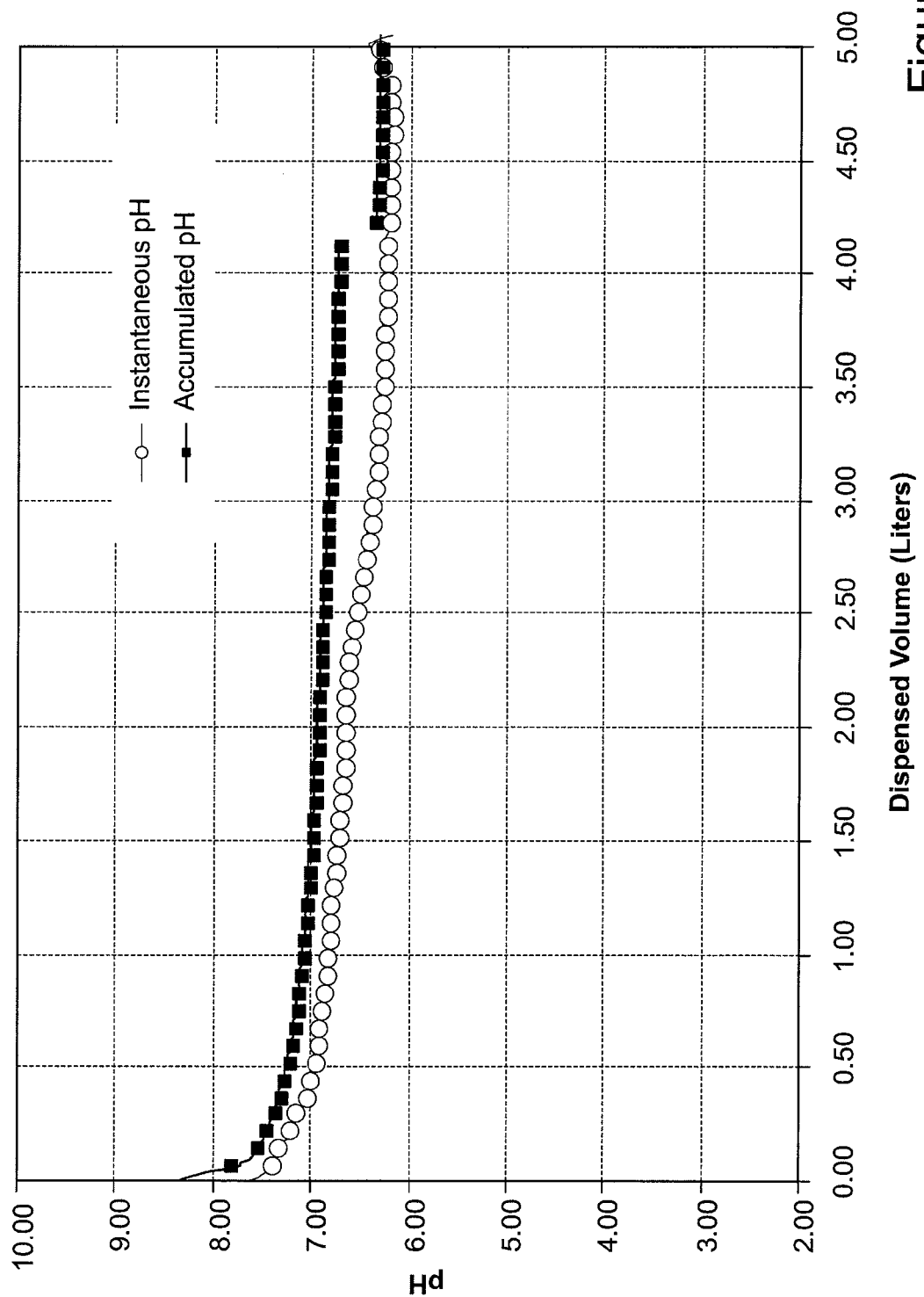
Figure 14C:
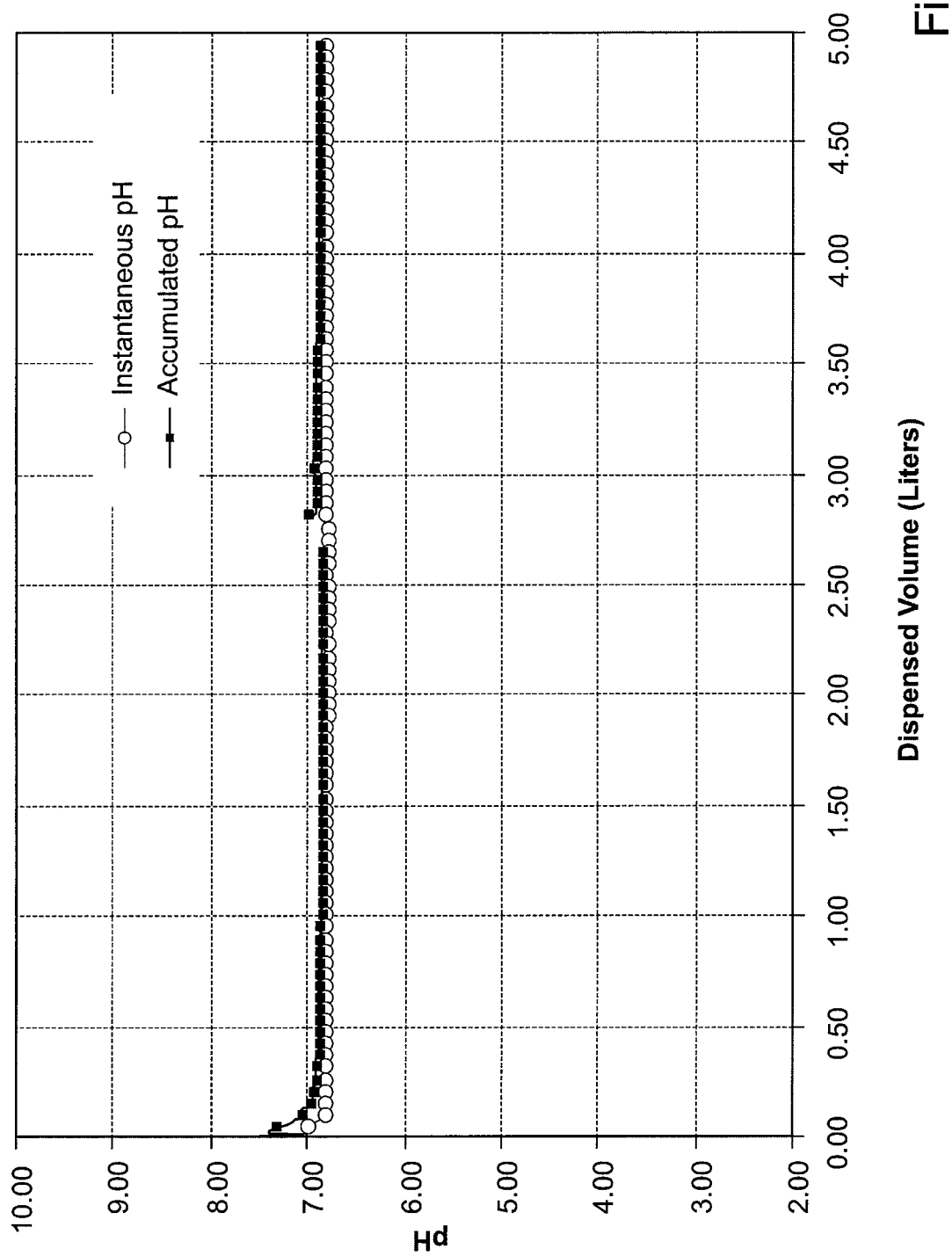
Figure 14D:
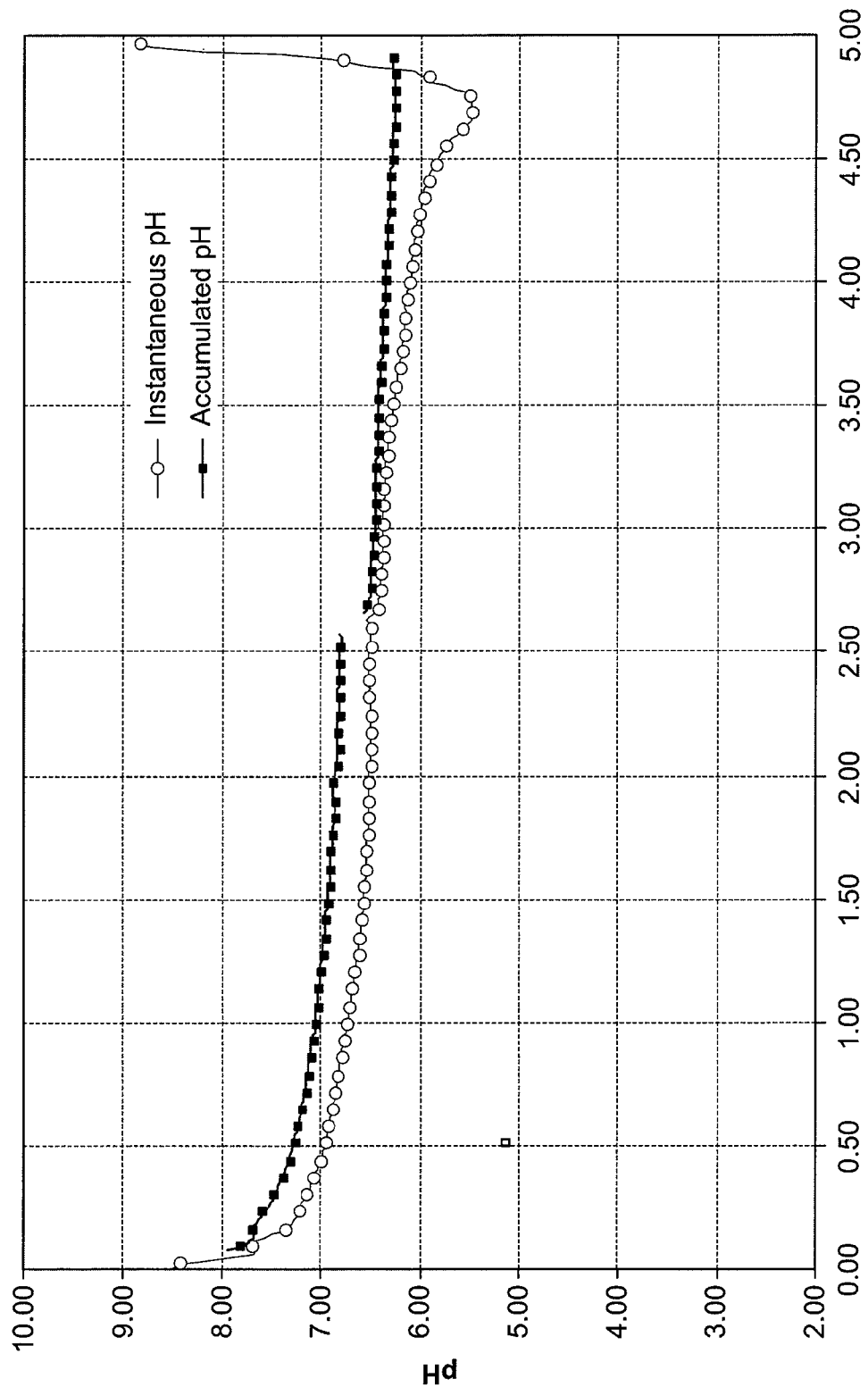
Figure 14E:
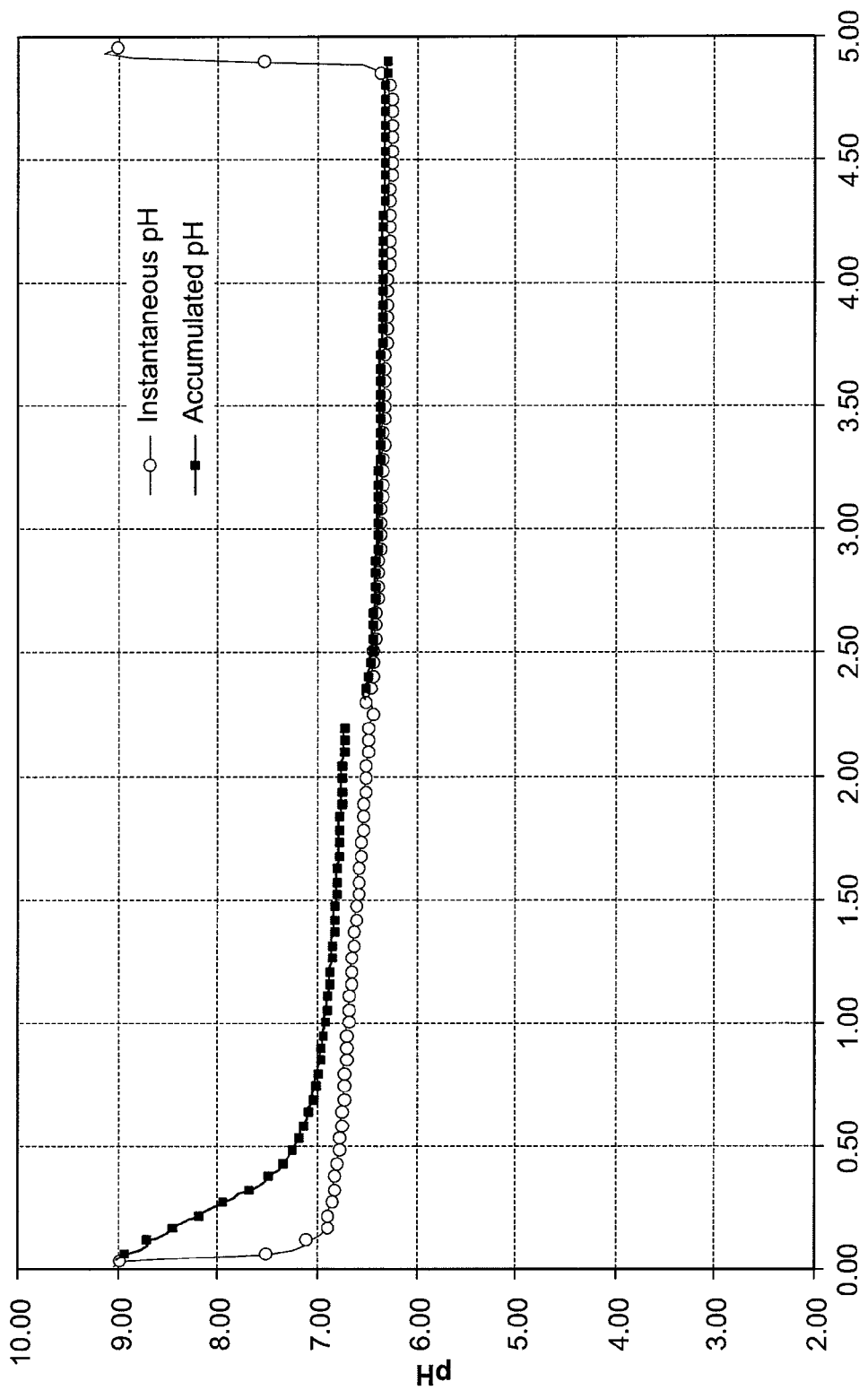

Referring to FIG. 13F, the patient or health care provider next grips the cover 53 (which is now repositioned over at least a portion of vessel 21) and grips the seal 26 with the other hand and bends to break the seal 26, thereby, opening a fluid pathway for outflow of the combined solutions 14, 22 (e.g., under gravity feed as effected by hanging system 10 and, significantly, vessel 12 vertically) via catheter 28 to the patient.

Of course, it will be appreciated that system 10 of FIGS. 12A-12E, as well of the other systems described herein, may be utilized with procedures other than those in FIGS. 13A-13F, as discussed more fully below. FIGS. 14A-14F are graphs depicting pH as a function of time of the outflow of catheter 28 for such alternate procedures for sample system(s) of the type shown in FIGS. 12A-12E when used with normally expected operating procedures (e.g., by way of non-limiting example, where vessel 21 is squeezed with at least a nominal squeezing force sufficient to achieve a fluid pressure of about 8 psi).

By way of non-limiting example, in one preferred such alternate procedure the steps shown in FIGS. 13B and 13C are carried out two times (rather than three times), and the step shown in FIG. 13D is carried out one time (rather than two times). A graph of pH as a function of time of the outflow volume of catheter 28 for sample system(s) of 5 L capacity of the type shown in FIGS. 12A-12E using this procedure is presented in FIG. 14A. In the sample system(s), the initial solution 14 in vessel 12 comprised dextrose, calcium chloride, magnesium chloride, and sodium chloride at pH 2.6-3.2, while the initial solution 22 in vessel 21 comprised sodium lactate and sodium bicarbonate at pH 9.2-9.4. By way of further non-limiting example, in another such alternate procedure the steps shown in FIGS. 13B and 13C were carried out two times with only nominal squeezing forces exerted on the vessel 21; inverting step shown in FIG. 13D was not carried out. A graph of pH as a function of the outflow volume of catheter 28 for sample system(s) of 5 L capacity of the type shown in FIGS. 12A-12E using this procedure, with a nominal squeezing force of about 8 psi, is presented in FIG. 14B; that for a nominal squeezing force of about 15 psi is presented in FIG. 14C. The sample system(s) were as describe in the preceding example.

By way of further non-limiting example, in another such alternate procedure the step shown in FIG. 13B was carried out one time with nominal squeezing forces exerted on vessel 21; the step shown in FIG. 13C was not carried out; and, the inverting step shown in FIG. 13D was not carried out. A graph of pH as a function of time of the outflow volume of catheter 28 for sample system(s) of 5 L capacity of the type shown in FIGS. 12A-12E using this procedure is presented in FIG. 14D. The sample system(s) were as describe in the preceding example.

By way of further non-limiting example, in another such alternate procedure the step shown in FIG. 13B was carried out one time with low pressure exerted on vessel 21; the step shown in FIG. 13C was not carried out; and, the inverting step shown in FIG. 13D was carried out one time. A graph of pH as a function of the outflow volume of catheter 28 for sample system(s) of 5 L capacity of the type shown in FIGS. 12A-12E prepared using this procedure is presented in FIG. 14E. The sample system(s) were as describe in the preceding example.

Figure 9:
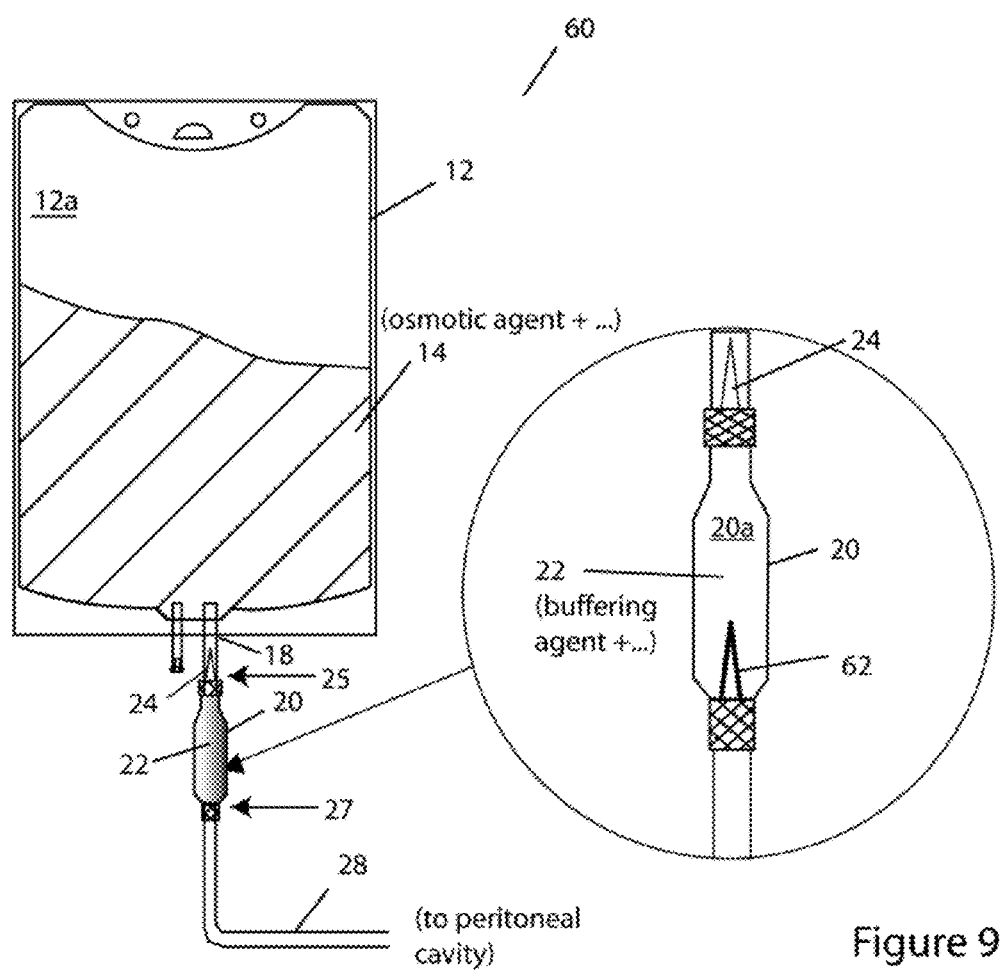
FIG. 9 illustrates an embodiment of the invention in which the fluid-filled second compartment defines the protective member.

Referring to FIG. 9, an alternate arrangement of the structures shown in FIG. 1 can further insure that the seals are broken in an order that prevents fluid transfer to the catheter 28 (and any downstream equipment) prior to mixing of the PD agents. That drawing depicts container system 60 of the same general configuration as container system 10 of FIG. 1 (as indicated by like reference numerals), albeit with the second seal (element 26 of FIG. 1, element 62 of FIG. 9) disposed within vessel 20 (e.g., rather than between the distal port of that vessel 20 and the catheter 28) so as to inhibit its manipulation and breaking until seal 24 is broken and fluid (or other) pressure within the vessel is reduced.

As with seal 26, seal 62 is a frangible member that can be fabricated from nylon, plastic, or other medical-grade material, and that can be formed in the configurations discussed above in connection with seal 24 (and shown, for example, in FIG. 5). Moreover, like seal 26, seal 62 can be disposed between the distal port of the vessel 20 and the catheter 28 and affixed to (and/or formed integrally with) an interior fluid-transfer path of one or both of those.

Preferably, however, seal 62 is disposed so as to inhibit it from being manipulated (and, more significantly, broken) when vessel 20 contains its post-manufacture complement of PD buffer agent solution 22 (and/or other liquids, gasses or solids). In the embodiment of FIG. 9, this is achieved by extending the seal 62 within the vessel 20, e.g., in the manner shown in FIG. 9, so as to inhibit squeezing, twisting or other manipulation of vessel 20, catheter 28 or otherwise from breaking seal 62 prior to breaking of seal 24 and (i) expulsion of at least some of its post-manufacturing complement of PD buffering agent 22 (and/or other liquids, gasses or solids)—and, preferably, expulsion of at least 10%-30% and, still more preferably, at least 30%-50% and, yet still more preferably, at least 50%—of such agent (and/or other liquids, gasses or solids) and/or (ii) reduction of the turgidity or other pressure effected within the vessel 20 by that agent 22 (and/or other liquids, gasses or solids). Those skilled in the art will appreciate that configurations of seal 62 other than that shown in FIG. 9 can be employed to this same end, as well.

In some embodiments of the invention, the seals 24, 62, are colored differently to alert and remind the user of the proper order in which they are to be broken. Those skilled in the art will appreciate, of course, that coloration can be used in connection with other elements of the system 10, as well.

FIGS. 10A-10D depict utilization of PD system 60, including seal 62, in a manner according to the invention.

Figure 10A:
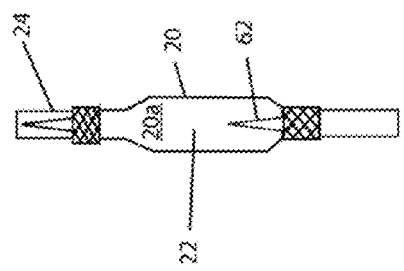
FIGS. 10A-10D illustrate operation of the system of FIG. 9.

Initially, as shown in FIG. 10A, seals 24, 26 are unbroken and compartment 20a contains its post-manufacture complement of buffer agent 22 (and/or other gasses, fluids, solids). Consistent with the discussion above, vessel 20 is under sufficient fluid (or other) pressure to inhibit squeezing, twisting or other manipulation of it sufficient to break seal 62.

Figure 10B:
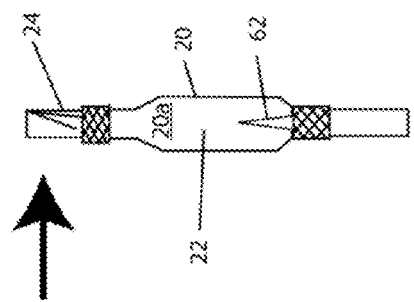
Figure 10C:
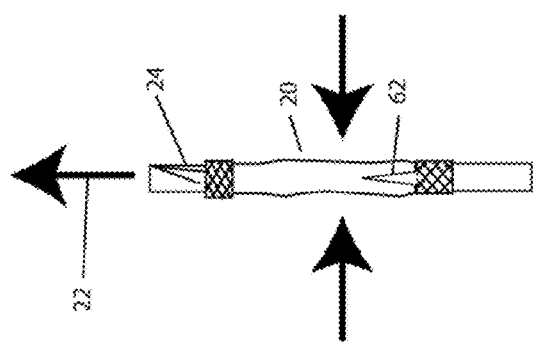

Referring to FIGS. 10B-10C, seal 62 remains intact while the user breaks seal 24 (e.g., by bending the proximal end of vessel 20 relative to port 18) and compresses vessel 20 in order to expel buffer agent 22 for mixing with osmotic agent 14.

Figure 10D:
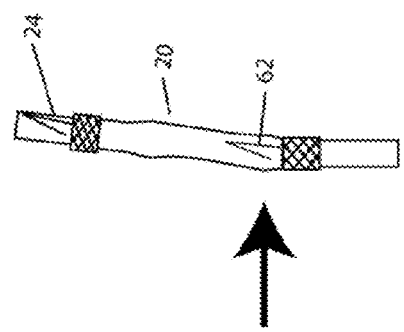

Referring to FIG. 10D, the user bends or otherwise manipulates vessel 20 in order to break seal 62, once the seal 24 has been broken and the pressure within vessel 20 has been reduced. Once that seal 62 is broken, the mixed PD constituents can pass to catheter 28 (and/or other downstream equipment).

Systems as described above (and below) can be used to contain, mix and dispense a variety of constitutes. In one embodiment, the first compartment houses a PD osmotic agent at physiological use concentrations, i.e., substantially at concentrations at which that agent will be introduced into the patient's abdomen. Those concentrations for example of dextrose is about 1.5%-4.25%, more preferably, about 2.0%-4.0% and, still more preferably, about 2.0%-3.0%. The PD osmotic agent is also at a physiologically low pH, i.e., a pH below that at which that agent will be introduced into the patient's abdomen, preferably, the pH is about 1.0-6.0 and, most preferably, about 1.0-3.0.

Examples of suitable PD osmotic agents include, but are not limited to, sugars such as glucose (e.g., dextrose), poly (glucose) (i.e., a polymer made from repeating glucose residues, e.g., icodextrin, made from repeating dextrose units), fructose, dextrans, polyanions, and the like. Other PD osmotic agents may be non-sugar osmotic agent that function as an equivalent could be a viable substitute, such as small amino acids.

In a preferred example, the PD osmotic agent is dextrose. The concentration of dextrose is about 1.5%-4.25%, more preferably, about 2.0%-4.0% and, still more preferably, about 2.0%-3.0%.

As used herein, "mEq/L" refers to the concentration of a particular PD solution component (solute) present in proportion to the amount of water present. More specifically, mEq/L refers to the number of milli-equivalents of solute per liter of water. Milli-equivalents per liter are calculated by multiplying the moles per liter of solute by the number of charged species (groups) per molecule of solute, which is then multiplied by a factor of 1,000. As an example, when 10 grams of citric acid are added to a liter of water, the citric acid is present at a concentration of 10 g/L. Anhydrous citric acid has a molecular weight of 192.12 g/mol; therefore, the number of moles per liter of citric acid, and consequently citrate anion (since there is one mole of citrate anion per mole of citric acid), is 10 g/L divided by 192.12 g/mol, which is 0.05 mol/L. Citrate anion has three negatively charged species in the form of carboxylate groups. Accordingly, the citrate concentration of 0.05 mol/L is multiplied by three and then by 1,000, in order to provide a concentration of citrate in terms of mEq/L, which in the present example is 156 mEq/L of citrate anion.

The same method of calculation can be used to determine the mEq/L of other agents such as lactate and dextrose. For example, 4.48 grams of sodium lactate (molecular weight of 112.1 gram/mol) per liter of water provides 40 mEq/L of sodium cations and 40 mEq/L of lactate anions. For dextrose, 42.5 grams of dextrose (molecular weight of 180.2 gram/mol) per liter of water provides 235.8 mEq/L of dextrose.

The PD osmotic agent can contain electrolytes, in addition to the osmotic agent. Suitable electrolytes may include, for example, sodium, potassium, calcium and magnesium. In the PD solution composition, the preferred concentration range for sodium is from about 100 to about 132 mEq/L. The preferred concentration range for potassium is less than about 3.50 mEq/L. The preferred concentration range for calcium is less than about 2.50 mEq/L. The preferred concentration range for magnesium is less than about 1.50 mEq/L.

The solution in the second container can be a concentrated agent and, specifically, in the illustrated embodiment (for example), a concentrated PD buffer solution. The term "concentrated" as used herein refers to an agent that is stronger than the chemically "Normal" concentration for that particular agent. The terms "Normal" and "Normal concentration" are used herein in the conventional sense of the chemical arts to refer to solutions having a concentration of 1 gram equivalent per liter of a solute. Thus, the Normal concentration of an ionic buffer agent is effectively equal to the molar concentration divided by the valence (the number of free or missing electrons) of the ion. For example, if a standard amount of a buffer agent is 60% (w/w), then 60 mls of that buffer agent would be added to one liter of water in order to obtain Normal concentration for that agent. In order to achieve a 10-fold increase in concentration (e.g., as in some embodiments of the invention), only 6 mls of the buffer is needed in one liter of solution.

The concentrated agent and, more specifically, the concentrated buffer utilized in systems and methods according to the invention can be of any concentration that is stronger than the chemically Normal concentration. For example, the concentrated buffer can be about 3-fold higher than Normal, 5-fold, 7-fold, 10-fold, 15-fold, and up to at least 50-fold higher than the Normal buffer. As those skilled in the art will appreciate, conventional, commercially available PD solutions, such as Deflex, by way of non-limiting example, are of chemically "Normal" concentration. Thus, the concentrated PD buffer agents utilized in embodiments of the present invention are of manifold increases in concentration relative to the commercial norm. The advantage of using concentrated buffers is that they can be stored and sterilized in small volume containers.

Alternatively, a sufficient quantity of buffer to produce a Normal concentration of a buffer upon mixing can be stored in a reduced volume. For example, a Normal amount of lactate buffer is typically 60% (w/w), i.e., 7.46 grams of sodium lactate buffer to one liter of solution. In this invention, the lactate buffer can be contained in the vessel 20 such that 7.46 grams of sodium lactate is contained in a vessel with a volumetric capacity of about 15 mls. The advantage of the invention is that the buffers can be contained and sterilized in small volume containers.

Examples of buffers include, but are not limited to, lactates, acetates, pyruvates, citrates, and the like. The lactate source may be any of lactic acid, sodium lactate, potassium lactate, calcium lactate, magnesium lactate, and the like. The acetate source may be any of acetic acid, sodium acetate, potassium acetate, calcium acetate, calcium acetate, magnesium acetate, and the like. Any or all of these chemicals are commercially available, in USP-grade if desired, from many chemical supply houses including, for example, Aldrich Chemical Co., Milwaukee Wis.

A preferred example of a PD buffer solution is a concentrated lactate buffer solution comprising lactate at a concentration of 20 milliequivalent per liter (mEq/l) to about 60 mEq/l, preferably a concentration of about 30 mEq/l to about 50 mEq/l, and most preferably, a concentration of 40 mEq/l. In addition, the lactate buffer solution may further comprise a bicarbonate at a concentration of about 5 mEq/l to about 10 mEq/l. A preferred buffer comprises 30-35 mEq/L of sodium lactate and 10-5.0 mEq/L of sodium bicarbonate.

The pH range of the PD osmotic agent solution is about 1.0-6.0 and, most preferably, between 1.0-3.0. The pH range of the PD buffer agent solution is about 8.0 to about 14.0, and, more preferably, a pH of about 9.0 to about 12 and, still more preferably, a pH of about 9.0 to about 10.0.

The different PD components can be dissolved in water that is essentially pyrogen-free and that at least meets the purity requirements established by United States Pharmacopia (USP)-grade for PD solutions.

A Normal PD solution typically comprises dextrose, sodium chloride, magnesium chloride and calcium chloride, sodium lactate, sodium hydroxide or hydrochloric acid added to adjust pH levels. The resulting pH of Normal PD solutions is about pH 5.0-6.0, which is less than optimum for blood, which has a pH of about 7.35 and 7.45. The Normal PD solutions often also contain GDPs. The seven commonly identified and published GDPs are acetaldehyde (AcA), 3-deoxglucosone (3-DG), 5-hydroxymethylfuraldehyde (5-HMF), glyoxal (Glx), methglyoxal (M-Glx), formaldehyde (FoA), and furaldehyde (FurA).

The systems and methods of the present invention provide PD solutions with reduced GDPs, as well as with more physiologically optimal concentrations and pH's. To this end, the PD osmotic agent solution and PD buffer agent are sterilized separately, thus, reducing the formation of degradation products that would otherwise result from the reaction of those agents at sterilization (or other high temperatures). The pH of the separate solutions is adjusted, moreover, in the illustrated embodiment, to further minimize GDP production during sterilization. That is to say the pH range of the PD osmotic agent solution is about 1.0-6.0 and, more preferably, between 1.0-3.0, while the pH range of the PD buffer agent solution is about 8.0 to about 14.0, and, more preferably, a pH of about 9.0 to about 12 and, still more preferably, a pH of about 9.0 to about 10.0. After sterilization, the buffer agent can be added to the osmotic agent solution, producing a mixed PD solution with a pH in the physiologically optimal range of about 5.0 to about 8.0 and, more preferably, about 6.0 to about 7.0, and, most preferably, about pH 7.2. As a result, systems and methods as described herein can provide PD solutions with an overall reduction in GDPs in the range of about 50% to about 80% compared with Normal PD solutions.

With continued reference to the drawings, in order to keep the PD osmotic and buffer agents separate prior to sterilization, vessels 12 and 20 are manufactured, shipped and stored with seals 24 and 26 intact. Those containers may be pre-assembled, e.g., so that they are available for use by a patient, health care provider or manufacturer in the configuration shown in FIG. 1 (not including attachment of catheter 28), or they may be manufactured, shipped and stored as kits, e.g., with the vessels 12 and 20 filled with their respective PD agents, but in unassembled form. The seal 24 may also be broken after sterilization at the time of manufacture.

Regardless, the vessels 12, 20 are sterilized before the seal 24 is broken and, therefore, before their respective contents have had a chance to mix. This is shown in step 30 of FIG. 2, which is a flow chart depicting a sequence for sterilizing and administering a PD solution according to the invention. This sterilization, which can be performed by the manufacturer and/or the health care provider, is achieved by steam-sterilization or other such conventional methods known in the art. Sterilization times and temperatures/pressures are in accord with those appropriate for the separated agents contained in vessels 12, 20, not reduced times and temperatures/pressures which might otherwise be necessary to prevent GDP build-up in sterilization of the combined components.

Figure 2:
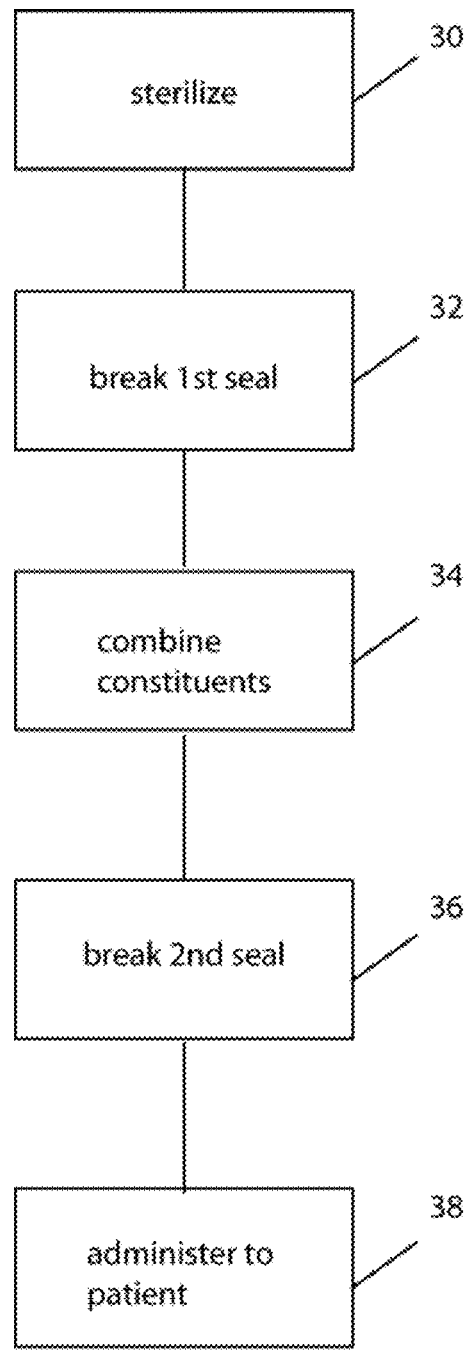
FIG. 2 depicts a sequence for sterilizing and administering a peritoneal dialysis solution according to the invention.

With continued reference to FIG. 2, step 32, following sterilization, seal 24 is broken (e.g., by squeezing and/or twisting of vessel 20 and/or port 18) to permit mixing of the PD buffer agent with the PD osmotic agent. The agents can be mixed by shaking, kneading or other action on the vessels 12, 20. See step 34. Thereafter, the solution is ready for administration—pending, for example, warming or other steps necessary for patient comfort or well being. To this end, seal 26 is broken, e.g., by squeezing or twisting of the distal port of vessel 20 and/or its interface with catheter 28. See step 36. Where a protective member (such as cover 52) is present, step 36 can further include the step of moving the protective member to allow access to, and breaking of, seal 26. Once seal 26 is broken, the PD solution can exit from the port into the catheter (and any downstream equipment) and, finally, to a patient. See step 38.

Figure 3:
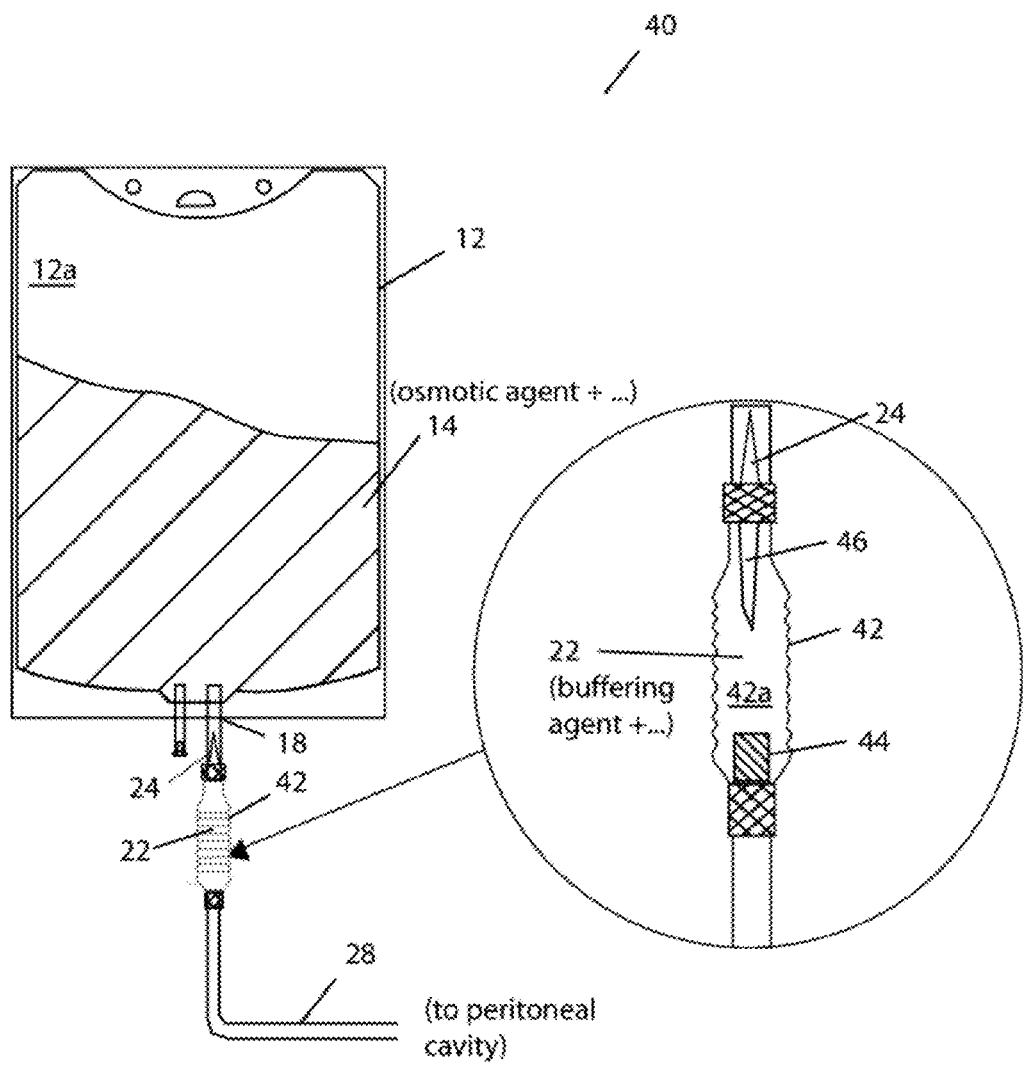
FIG. 3 depicts a system for containing a peritoneal dialysis solution according to a further practice of the invention and includes a break-out portion depicting one of the vessels of that system in greater detail.

FIG. 3 depicts system 40 according to a further embodiment of the invention generally constructed and utilized (as indicated by like reference numerals) as system 10, described above. Differences in construction and utilization are discussed in the text that follows and are evident in the drawings.

Vessel 42 of system 40 comprises compartment 42a for, by way of example, PD buffer agent solution 22, as generally described above. Compartment 42a and vessel 42 are collapsible—i.e., they are configured such that force applied thereto, e.g., by a patient, health care provider or other, causes the volume of compartment 42a to at least temporarily decrease so as to expel fluid contained therein. To this end, in the illustrated embodiment, vessel 42 has fan-fold walls, or bellows, along an axis aligned with a direction of fluid expulsion—here, along the fluid transfer path between vessel 42 and vessel 12. Other embodiments may utilize walls of other construction to facilitate collapse along the same or other axes. Regardless, those walls are preferably sufficiently durable to prevent leakage, e.g., so that after fluid expulsion, the compartment 42a can form part of a fluid transfer path between the compartment 12a and the patient's peritoneal cavity.

Illustrated vessel 42 may be fabricated from PVC, polyolefin, polypropylene, rubber and/or other medical grade materials suitable for forming a collapsible container as described herein. As with vessel 20 (FIG. 1), above, vessel 42 can be formed, e.g., by blow molding, dip-forming, or otherwise.

As above, seal 24 is adapted to prevent fluid transfer (or other contact) between the PD agents contained in the compartments during manufacture, transport, storage and sterilization of system 40, yet, to permit such fluid transfer upon squeezing, twisting or other manipulation of vessel 42 and/or port 18 by a patient, health care provider, or manufacturer, e.g., following sterilization.

Like seal 26 of systems 10 and 50 (FIGS. 1 and 6), seal 44 of system 40 is adapted to prevent fluid transfer to the catheter 28 (and any downstream equipment) prior to sterilization and mixing of the PD agents. However, unlike seal 26, seal 44 (which, too, is disposed at the distal port of the vessel 42) is broken by a further member 46 that is disposed in compartment 42a and that pierces, cuts or otherwise breaks seal 44 when the vessel 42 and compartment 42a have been compressed sufficiently to insure expulsion of the fluid 22 into compartment 12a.

Seal 44 can be formed of PVC, polyolefin, polypropylene, rubber and/or other medical grade materials suitable for preventing fluid transfer, e.g., during manufacture, shipping, storage, sterilization, but susceptible to being broken, e.g., by member 46 as described here, following sterilization and mixing of the agents 14, 22.

In the illustrated embodiment, member 46 is depicted as a bayonet, though in other embodiments it may be of another shape. It can be constructed of the same materials utilized, e.g., for element 24. Member 46 can be formed near the proximal port of vessel 42 (e.g., opposite seal 24) and affixed to (and/or formed integrally with) an interior fluid-transfer path between the vessels, as shown, though in other embodiments it may be disposed elsewhere, e.g., preferably so that it breaks member 44 upon sufficient compression of vessel 42 and compartment 42a. To this end, in the illustration, member 46 is of such length that its tip (for piercing seal 44) is disposed approximately 40% from the proximal end of compartment 42a. In other embodiments, the member may be of other lengths, depending upon the compressibility of compartment 42a and on the desired degree of expulsion of fluid 22 from compartment 42a to compartment 12a prior to piercing of seal 44.

As above, the container system 40 permits the PD osmotic agent solution and PD buffer agent to be sterilized separately, thus, reducing the formation of degradation products that would otherwise result from the reaction of the osmotic agent with the buffer agent at high temperature. To this end, the vessels 12 and 42 are manufactured, shipped and stored with seals 24 and 44 intact. Those containers may be pre-assembled, e.g., so that they are available for use by a patient or health care provider in the configuration shown in FIG. 3 (not including attachment of catheter 28), or they may be manufactured, shipped and stored as kits, e.g., with the vessels 12 and 42 filled with their respective PD agents, but in unassembled form. As noted above, the seal 24 may also be broken after sterilization at the time of manufacture.

Regardless, as above, the vessels 12, 42 are sterilized before the seal 24 is broken and, therefore, before their respective contents have had a chance to mix. Such sterilization may be accomplished as described above, e.g., in connection with step 30 of FIG. 2.

Figure 4A:
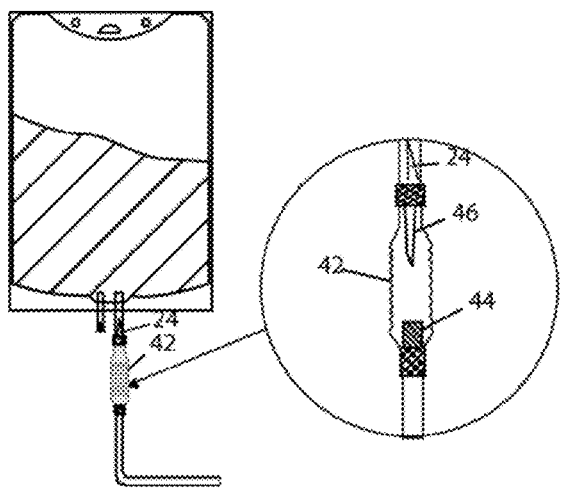
FIGS. 4A-4C depict utilization of the system of FIG. 3 to mix agents of the peritoneal dialysis solution (e.g., following sterilization) and to transfer the mixed agents to the patient.
Figure 4B:
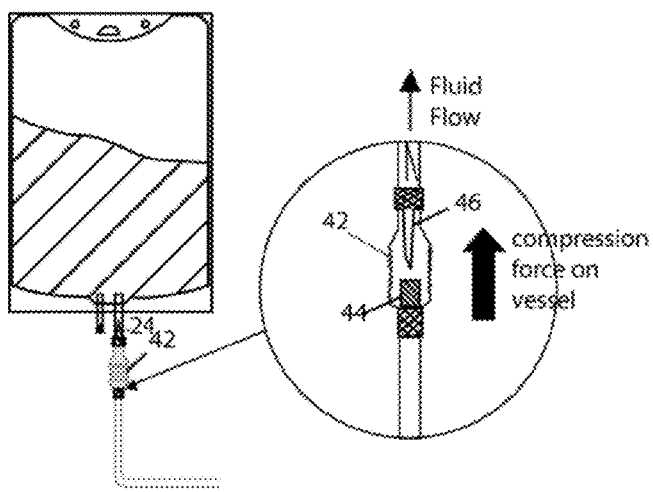

Following sterilization, a factory worker, health care provider, a patient, or other, breaks seal 24 (e.g., by squeezing and/or twisting of vessel 42 and/or port 18); see, FIG. 4A. He or she then compresses (or collapses) vessel 42 to expel agent 22 from compartment 42a into compartment 12a, thereby, facilitating its mixing with agent 14; see, FIG. 4B.

Figure 4C:
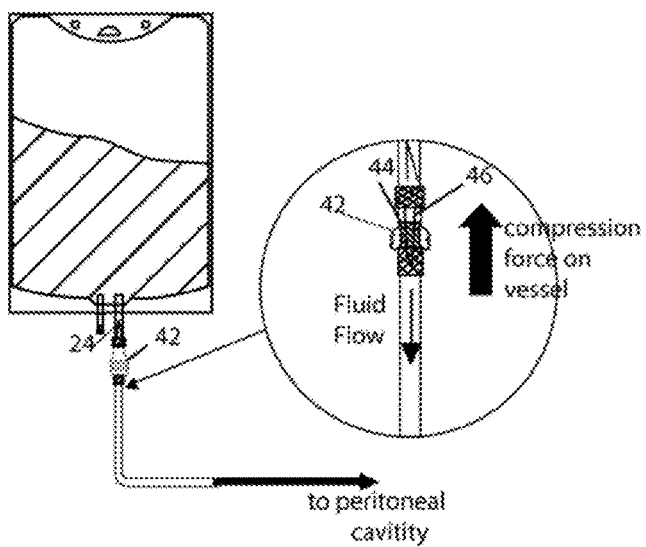

The factory worker, health care provider, patient or other continues compressing (or collapsing) vessel 42 until the tip of member 46 contacts and breaks seal 44; see, FIG. 4C. This allows the PD solution to exit from the port into the catheter (and any downstream equipment) and, finally, to a patient.

It will be appreciated that systems and methods according to the invention are applicable to a range of peritoneal dialysis applications and other medical applications in which at least one agent (or combination of agents) requires separate sterilization prior to combination with another agent (or combination thereof). According to conventional practice, such agents are sometimes combined prior to sterilization or, if combined after sterilization, for example, by injecting one of them into a medication port of a container that holds the other agent. The former increases risk of degradation of the agents. The latter increases the risk to health care personnel and/or the patient. Systems and methods of the invention avoid these risks and other shortcomings of the prior art by allowing the agent(s) to be sterilized separately and, then, combined, e.g., without the use of needles or other mechanisms that are expensive, unwieldy, and/or place the agent(s), health care personnel and/or patients at risk.

Another advantage of systems and methods of the invention, is that depending on the requirements of the agent that will be added to the medical solution, the second vessel can be coated with materials that maintain the shelf life and/or stability of the agent or additive. Examples of additives that can be administered with this invention are amino acids, proteins, heparin, and vitamins.

As evident in the examples below, systems and method of the invention have been used to prepare PD solutions with reduced GDPs and a more physiologically optimal pH levels.

TABLE 1

Samples Preparation

| Label | pH Adjusted To | mL of 1.0 M HCl per Liter of Solution | WFI | Glucose | $CaCl_2*2H_2O$ | $MgCl_2*2H_2O$ | NaCl |
|---|---|---|---|---|---|---|---|
| 1 | 3.0 | 1.37 | 80 L | 3,400 g | 14.72 g | 4.072 g | 430.16 g |
| 2 | 4.0 | 0.37 | | | | | |
| 3 | 4.5 | 0.27 | | | | | |
| 4 | 5.2 | 0.18 | | | | | |
| Buffer | | Straight Lactate Syrup up to 1000 g in a 1-Liter Bag | | | | | |

Table 1 shows sample preparations with the PD solutions constituents at different pH values. The sample labeled "Buffer" has concentrated lactate buffer solution added to it.

Table 2 shows the results of HPLC analysis of the samples to examine the various degradation products. The seven degradation products that were analyzed are as follows: acetaldehyde (AcA), 3-deoxglucosone (3-DG), 5-hydroxymethylfuraldehyde (5-HMF), glyoxal (Gix), methglyoxal (M-Gix), formaldehyde (FoA), and furaldehyde (FurA). The data from Table 2 shows that GDPs formation around pH 3.0 is the lowest among the solutions prepared and the Normal/commercial products. Sodium lactate as a buffer agent in PD solutions results in acetaldehyde (AcA) formation (See column entitled "pH" in Table 2). The results also demonstrate the effectiveness of reducing AcA formation by separating sodium lactate from the rest of the PD solution for steam sterilization. By adding sodium lactate buffer solution to the main PD solution at pH 3.0 (group 1), the resulting mixed PD solution has a pH of 5.2, which is the same as Normal PD solutions (referred to as "Delflex" in Table 2), but with significantly reduced GDPs than Normal PD solutions. This data demonstrates that reduced GDPs are obtained under current formulation and pH levels using the system of the invention. The data also shows that PD formulations with reduced GDPs are obtained at a physiological of around pH 7.0 (Table 4). Thus, the systems and methods of the invention provide significantly reduce GDPs in PD solutions that contain dextrose as an osmotic agent and sodium lactate as buffer.

hydrochloric acid to adjust the pH to 3.0. In one example, the vessel 20 is filled with a concentrated PD lactate buffer solution with lactate only, adjusted to a pH of about 10.0 to about 12.0. Sodium hydroxide can be used to adjust the pH of the lactate buffer. A suitable concentration of lactate buffer is 40 mEq/l lactate buffer. In another example, the second vessel 20 is filled with a concentrated PD lactate buffer solution comprising a bicarbonate buffer, adjusted to a pH of about 8.0 to

TABLE 2

GDPs results from HPLC Analysis

| Label | pH | Cl (mEq/L) | 3-DG (μmol/L) | AcA (μmol/L) | 5-HMF (μmol/L) | Gix (μmol/L) | M-Gix (μmol/L) | FoA (μmol/L) | FurA (μmol/L) |
|---|---|---|---|---|---|---|---|---|---|
| Buffer | 8.1 | — | ND | 15 | ND | ND | ND | 3 | ND |
| 1-A | 3.0 | — | 37 | ND | ND | ND | 7 | ND | ND |
| 1-B | 3.0 | — | 119 | ND | 18 | ND | 8 | ND | ND |
| 1-C | 3.0 | — | 115 | 2 | 23 | ND | 7 | ND | ND |
| 1-D | 3.0 | — | 119 | 1 | 22 | ND | 9 | ND | ND |
| 2-A | 4.0 | — | 65 | ND | ND | ND | 9 | ND | ND |
| 2-B | 4.0 | — | 299 | ND | 39 | ND | 8 | 1 | ND |
| 2-C | 4.0 | — | 299 | ND | 38 | ND | 13 | ND | ND |
| 2-D | 4.0 | — | 248 | ND | 34 | 0.2 | 8 | ND | ND |
| 3-A | 4.7 | — | 91 | ND | ND | ND | 9 | ND | ND |
| 3-B | 4.4 | — | 526 | 0.1 | 45 | 0.5 | 9 | ND | ND |
| 3-C | 4.4 | — | 532 | ND | 46 | ND | 9 | ND | ND |
| 3-D | 4.4 | — | 513 | ND | 46 | 0.7 | 14 | ND | ND |
| 4-A | 5.5 | — | 112 | ND | ND | 0.2 | 7 | ND | ND |
| 4-B | 4.5 | — | 699 | ND | 54 | 0.7 | 8 | ND | ND |
| 4-C | 4.5 | — | 653 | ND | 51 | 1.6 | 11 | ND | ND |
| 4-D | 4.5 | — | 649 | 0.2 | 44 | 0.6 | 8 | 3 | ND |
| 1-A (buffered) | 5.3 | 95.5 | 45 | 6 | ND | ND | 9 | ND | ND |
| 1-B (buffered) | 5.3 | 95.6 | 131 | 16 | 26 | ND | 8 | ND | ND |
| 1-C (buffered) | 5.3 | 94.8 | 128 | 15 | 25 | ND | 9 | ND | ND |
| 1-D (buffered) | 5.3 | 95.4 | 134 | 15 | 25 | ND | 10 | ND | ND |
| 2-A (buffered) | 6.1 | 95.7 | 90 | 6 | ND | ND | 10 | ND | ND |
| 2-B (buffered) | 6.1 | 95.2 | 316 | 20 | 39 | ND | 7 | ND | ND |
| 2-C (buffered) | 6.1 | 95.3 | 307 | 19 | 40 | ND | 11 | ND | ND |
| 2-D (buffered) | 6.1 | 95.0 | 303 | 2 | 35 | ND | 9 | ND | ND |
| 3-A (buffered) | 6.4 | 95.1 | 95 | 10 | ND | 0.5 | 11 | ND | ND |
| 3-B (buffered) | 6.3 | 95.3 | 570 | 18 | 46 | 0.3 | 7 | ND | ND |
| 3-C (buffered) | 6.3 | 95.1 | 537 | 3 | 45 | 0.5 | 13 | ND | ND |
| 3-D (buffered) | 6.3 | 95.4 | 560 | 20 | 45 | ND | 7 | ND | ND |
| 4-A (buffered) | 6.6 | 95.4 | 121 | 7 | ND | 0.4 | 10 | ND | ND |
| 4-B (buffered) | 6.3 | 95.0 | 650 | 16 | 52 | ND | 9 | ND | ND |
| 4-C (buffered) | 6.3 | 95.8 | 668 | 3 | 50 | 1.7 | 13 | ND | ND |
| 4-D (buffered) | 6.3 | 96.2 | 685 | 19 | 50 | 0.7 | 10 | 4 | ND |
| 4.25% Delfex | 5.2 | 95 | 348 | 323 | 38 | 4 | 25 | 12 | ND |
| 4.25% Balance | 7.0 | — | 175 | 49 | 12 | 4 | 14 | 4 | ND |

In some embodiments of the invention, the PD solutions are produced with reduced GDPs by using a buffer solution with a bicarbonate (e.g., sodium bicarbonate). The first vessel 12 contains a PD osmotic agent solution with dextrose, sodium chloride, magnesium chloride, calcium chloride, and about 9.0. Suitable concentrations are, 37 mEq/l lactate buffer with 3 mEq/l bicarbonate buffer.

The results obtained by using the methods and compositions of the present invention using buffer solutions are summarized in Tables 3 and 4.

TABLE 3

Formulation Comparison as Delivered to a Patient
FORMULATION, LowCA

| | PVC Product Design with Bubble | Bubble (mini-bag) Vol [m/l] | Soln pH | lactate [mEq/l] | bicarb or NaOH [mEq/l] | total buffer [mEq/l] | Na [mEq/l] | Cl [mEq/l] | Mg [mEq/l] | Dextrose [%] |
|---|---|---|---|---|---|---|---|---|---|---|
| 1 | Neutral pH PD solution, lactate/NaOH in bubble | 6.7 | 7.4 | 38.04 | 1.06 of NaOH | 40 | 132 | 95 | 0.5 | 1.50% 4.25% |
| 2 | Neutral pH PD solution; lactate/ | 10 | 7.4 | 37 | 3 of sodium | 40 | 132 | 95 | 0.5 | 1.50% 4.25% |

TABLE 3-continued

Formulation Comparison as Delivered to a Patient
FORMULATION, LowCA

| PVC Product Design with Bubble | Bubble (mini-bag) Vol [m/l] | Soln pH | lactate [mEq/l] | bicarb or NaOH [mEq/l] | total buffer [mEq/l] | Na [mEq/l] | Cl [mEq/l] | Mg [mEq/l] | Dextrose [%] |
|---|---|---|---|---|---|---|---|---|---|
| bicarb buffer in bubble | | | | biacarbonate | | | | | |
| 3 Delflex (current Product as reference) | NA | 5.3 | 40 | 0 | 40 | 132 | 95 | 0.5 | 1.50% 4.25% |
| 4 Balance (as reference only) | NA | 7.0 | 40 | 0 | 40 | 134 | 101.5 | 1.0 | 1.50% 4.25% |

Table 4 shows the results of an average of 3 samples. The concentrated PD lactate buffer was mixed with PVC bag contents containing the PD osmotic agent solution post sterilization. After combining the PD lactate buffer with the PD osmotic agent buffer, the resulting PD solution was examined and had a significantly reduced amount of AcA compared with the existing commercially available PD solutions referred to as "Deflex" and "Balance." Also, by maintaining the pH of the PD osmotic solution at 3.0 and then by adding concentrated PD lactate buffer at a pH of 10.0 to 12.0, the final pH of the resulting PD solution was at a more physiologically optimal pH of 7.2 (Table 4).

TABLE 4

GDP Results

| | GDPs (μmole/L) | | | |
|---|---|---|---|---|
| | Delflex (4.25%) | Balance (4.25%) | pH 3 Dextrose-side | pH 3 Dextrose-side |
| pH (Final, Mixed) | 5.2 | 6.9 | 5.3 | 7.1 |
| Buffer | Lactate | Lac/bic | Lactate only | Lactate/NaOH |
| 3-DG | 348 | 175 | 131 | 106 |
| AcA | 323 | 49 | 15 | 13 |
| 5-HMF | 38 | 12 | 25 | 28 |
| Glx | 4 | 4 | ND | 1 |
| M-Glx | 25 | 14 | 9 | 8 |
| FoA | 12 | 2 | ND | 1 |
| Reduction Ratio (%) | 0% | 65% | 76% | 80% |

Collectively, these demonstrate that by sterilizing a concentrated PD lactate buffer separately from the PD osmotic agent, and then adding the concentrated PD lactate buffer just before use, the amount of GDPs are significantly reduced. In addition, the resulting PD solution has a near neutral pH of about 7.4 optimized for peritoneal dialysis. Furthermore, the concentrated PD lactate buffer may also contain bicarbonate. When the PD lactate-bicarbonate buffer was added to the PD osmotic agent solution, the resulting PD solution also had significantly reduced GDPs, and a near neutral pH of about 7.4.

Described above are systems and method meeting the desired objects, among others. It will be appreciated that the embodiments illustrated and described herein are merely examples of the invention and that other embodiments, incorporating changes thereto, fall within the scope of the invention. Thus, by way of non-limiting example, it will be appreciated that although the first and second agent-containing compartments of the illustrated embodiments are shown as carrying agents of medical PD solutions), in other embodiments those compartments may contain agents of other medical or non-medical solutions. Moreover, it will be appreciated that, by way of further non-limiting example, although the text above describes breaking of the temporary seals (e.g., seals 24, 26, 44, 62) by manual manipulation, e.g., of the vessel 20, other embodiments may be adapted for breaking of those seals by automated apparatus (e.g., manipulation of the vessel or mini-tube 20 by robotic equipment or otherwise). In this context, what we claim is:

The invention claimed is:

1. A vessel comprising:
a first compartment containing a first agent of a solution,
a second compartment containing a second agent of the solution, the second compartment being in any of direct and indirect fluid coupling with the first compartment,
at least one of the first and second compartments being adapted to be manipulated at least partially independently of the other of said first and second compartments,
a first seal preventing fluid transfer between the first compartment and the second compartment, and
a second seal preventing fluid transfer between the second compartment and an outlet fluid pathway of the system,
a protective member coupled to the vessel configured to inhibit breaking of the second seal prior to breaking of the first seal.

2. The vessel of claim 1 adapted to insure expulsion of at least a portion of the second agent from the second compartment to the first compartment prior to breakage of the second seal.

3. The vessel of claim 2, wherein the first chamber and second chamber of the vessel are formed by any one of cutting, welding, stamping, and gluing a sheet or web of material.

4. The vessel of claim 3, wherein one or more regions of the vessel that define the first chamber and second chamber, respectively, are separably affixed to one another by any of perforations and tacks.

5. The vessel of claim 4, wherein any of said perforations and tacks are adapted to be breakable by manipulation by a patient, health care provider, or other.

6. The vessel of claim 2, further comprising a diffuser adapted to facilitate mixing of the first agent and the second agent upon expulsion of the second agent from the second compartment.

7. The vessel of claim 1, wherein the protective member is slidably disposed on the system and adapted to move from a first position, wherein the protective member inhibits breaking of the second seal, to a second position, wherein the protective member does not inhibit breaking of the second seal.

8. The vessel of claim 7, wherein, prior to breaking of the first seal, movement of the protective member from the first position to the second position is restrained by the second compartment.

9. The vessel of claim 8, wherein presence of a quantity of fluid in the second compartment inhibits the protective member from sliding to the second position.

10. A container system for storing a plurality of fluids, comprising:
- a vessel having a first chamber and a second chamber, the second chamber being in any of direct and indirect fluid coupling with the first chamber;
- a first seal preventing fluid transfer between the first chamber and the second chamber;
- a second seal preventing fluid transfer between the second chamber and an outlet fluid pathway of the container system;
- a protective member configured to inhibit breaking of the second seal prior to breaking of the first seal; and
- a port fluidly coupling the first chamber and the second chamber, the port comprising the first seal and a diffuser, the diffuser adapted to facilitate mixing of fluids upon expulsion of fluid from the second chamber to the first chamber.

11. The container system of claim 10, wherein the protective member has a slot or other opening sized to slide over at least a portion of the container forming the second chamber.

12. The container system of claim 11, wherein the slot or other opening is arranged to slide over at least the portion of the container forming the second chamber only after a quantity of fluid originally present in the second chamber has been expelled therefrom.

13. The container system of claim 11, wherein the slot or other opening is arranged to slide over at least the portion of the container forming the second chamber only if the second chamber is at least partially folded.

* * * * *